(12) United States Patent
Hattori et al.

(10) Patent No.: US 6,437,146 B1
(45) Date of Patent: Aug. 20, 2002

(54) OXAZOLE COMPOUNDS AS PROSTAGLANDIN $E_2$ AGONISTS OR ANTAGONISTS

(75) Inventors: Kouji Hattori; Akira Tanaka, both of Takarazuka; Yutaka Kono, Ibaraki; Shoko Nakazato, Nishinomiya, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/787,433

(22) PCT Filed: Sep. 24, 1998

(86) PCT No.: PCT/JP99/05212

§ 371 (c)(1),
(2), (4) Date: Apr. 20, 2001

(87) PCT Pub. No.: WO00/18744

PCT Pub. Date: Apr. 6, 2000

(30) Foreign Application Priority Data

Sep. 25, 1998 (AU) ................................................ PP6176
Apr. 19, 1999 (AU) ................................................ PP9822

(51) Int. Cl.[7] ..................... C07D 263/36; A61K 31/422
(52) U.S. Cl. ........................................ 548/236; 514/471
(58) Field of Search ........................... 548/236; 514/471

(56) References Cited

U.S. PATENT DOCUMENTS

| 3,901,908 A | | 8/1975 | Fitzi et al. |
| 5,187,188 A | * | 2/1993 | Meanwell .................... 514/374 |
| 5,262,540 A | * | 11/1993 | Meanwell .................... 514/374 |
| 5,362,897 A | * | 11/1994 | Meanwell .................... 548/236 |
| 5,892,099 A | | 4/1999 | Maruyama et al. |
| 6,043,275 A | | 3/2000 | Maruyama et al. |
| 6,245,790 B1 | | 6/2001 | Hattori et al. |

FOREIGN PATENT DOCUMENTS

| EP | 0 855 389 | 7/1998 |
| EP | 0 985 663 | 3/2000 |
| WO | WO 95/17393 | 6/1995 |
| WO | WO 97/03973 | 2/1997 |
| WO | WO 98/55468 | 12/1998 |
| WO | WO 99/21843 | 5/1999 |
| WO | WO 00/16760 | 3/2000 |

\* cited by examiner

*Primary Examiner*—Floyd D. Higel
*Assistant Examiner*—Golam M. M. Shameem
(74) *Attorney, Agent, or Firm*—Oblon, Spivak, McClelland, Maier & Neustadt, P.C.

(57) ABSTRACT

Oxazole compounds of formula (I), wherein $R^1$ is aryl which may be substituted with halogen(s), $R^2$ is aryl which may be substituted with halogen(s), X is single bond, (a) or $SO_2$, $R^3$ and $R^4$ are independently hydrogen or suitable substituent, (wherein X is (a), neither $R^3$ nor $R^4$ is hydrogen), $R^3$ and $R^4$ may be linked together to form (b), (b) is N-containing heterocyclic group which may be substituted with one or more suitable substituent(s), $R^5$ is hydrogen, etc., $A^1$ is lower alkylene or single bond, (c) is cyclo($C_3$–$C_9$)alkane or cyclo($C_5$–$C_9$)alkene, or a pro-drug thereof, or a pharmaceutically acceptable salt thereof, which are useful as medicament.

15 Claims, No Drawings

OXAZOLE COMPOUNDS AS PROSTAGLANDIN E$_2$ AGONISTS OR ANTAGONISTS

This application is a 371 of PCT/JP99/05212 Sep. 26, 1999.

TECHNICAL FIELD

This invention relates to prostaglandin E$_2$ agonist or antagonist such as oxazole compounds and pharmaceutically acceptable salts thereof which are useful as a medicament.

BACKGROUND ART

Some oxazole compounds are known, for example, in WO 95/17393, WO 95/24393 and WO 97/03973.

DISCLOSURE OF INVENTION

This invention relates to oxazole compounds. More particularly, this invention relates to oxazole compounds and pharmaceutically acceptable salts thereof which are useful as prostaglandin E$_2$ (hereinafter described as PGE$_2$) agonist or antagonists.

Accordingly, one object of this invention is to provide new and useful oxazole compounds and pharmaceutically acceptable salts thereof.

Another object of this invention is to provide processes for preparing of the oxazole compounds or pharmaceutically acceptable salts thereof.

A further object of this invention is to provide a pharmaceutical composition containing, as an active ingredient, said oxazole compounds or pharmaceutically acceptable salts thereof.

A still further object of this invention is to provide use of the oxazole compounds and pharmaceutically acceptable salts thereof for the manufacture of medicaments for treating or preventing PGE$_2$ mediated diseases.

A still more further object of this invention is to provide use of prostaglandin E$_2$ antagonist (especially, EP4 receptor blocker) such as oxazole compounds and pharmaceutically acceptable salts thereof for the manufacture of medicaments for treating or preventing mesangial proliferative glomerulonephritis.

The oxazole compounds of this invention can be represented by the following formula (I):

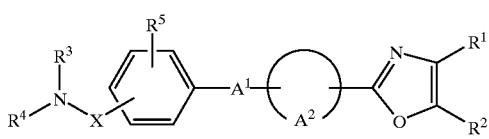

(1)

wherein
R$^1$ is aryl which may be substituted with halogen(s),
R$^2$ is aryl which may be substituted with halogen(s),
X is single bond

or SO$_2$,

R$^3$ and R$^4$ are independently hydrogen or suitable substituent, (wherein X is

neither R$^3$ nor R$^4$ is hydrogen),
R$^3$ and R$^4$ may be linked together to form

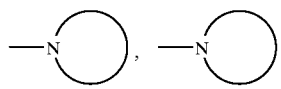

is N-containing heterocyclic group which may be substituted with one or more suitable substituent(s),
R$^5$ is
(1) hydrogen,
(2) hydroxy,
(3) carboxy, or
(4) protected carboxy,
A$^1$ is lower alkylene or single bond,

is cyclo(C$_3$–C$_9$)alkane or cyclo(C$_5$–C$_9$)alkene, or a pro-drug thereof, or a pharmaceutically acceptable salt thereof.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and a salt thereof can be in a form of a solvate, which is included within the scope of the present invention. The solvate preferably include a hydrate and an ethanolate.

Also included in the scope of invention are radiolabelled derivatives of compounds of formula (I) which are suitable for biological studies, and any form of the crystal of the compound (I).

According to the present invention, the oxazole compounds (I) or a pharmaceutically acceptable salt thereof can be prepared by the following Processes 1 to 5.

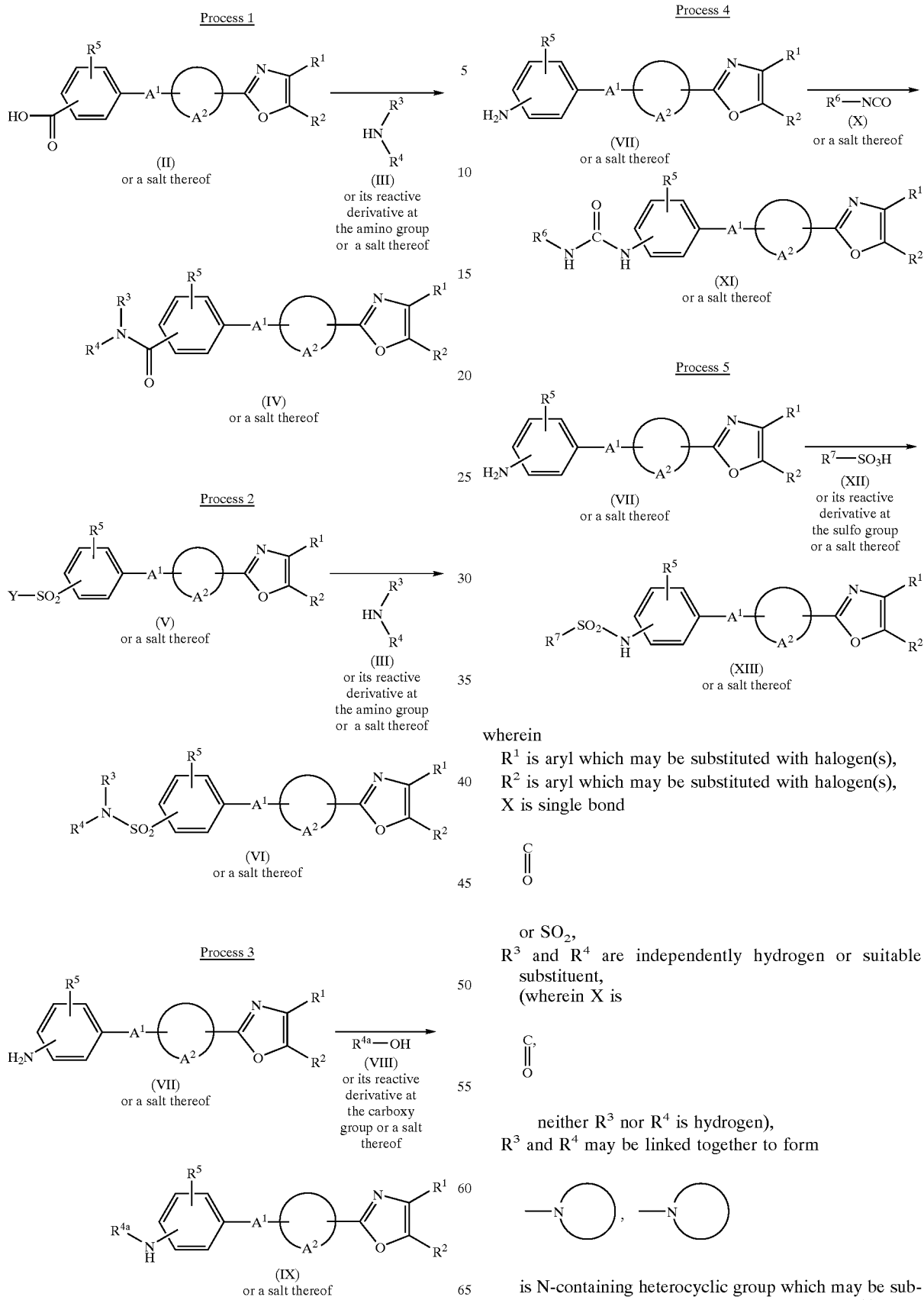

wherein
R[1] is aryl which may be substituted with halogen(s),
R[2] is aryl which may be substituted with halogen(s),
X is single bond

or SO$_2$,
R[3] and R[4] are independently hydrogen or suitable substituent,
(wherein X is

neither R[3] nor R[4] is hydrogen),
R[3] and R[4] may be linked together to form

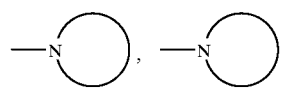

is N-containing heterocyclic group which may be substituted with one or more suitable substituent(s),
R[4a] is acyl which may be substituted with aryl, R⁵ is
(1) hydrogen,
(2) hydroxy,
(3) carboxy, or
(4) protected carboxy, R⁶ is acyl or hydroxy, R⁷ is lower alkyl, ar(lower)alkyl or aryl, A¹ is lower alkylene or single bond,

is cyclo(C₃–C₉)alkane or cyclo(C₅–C₉)alkene,

The starting compounds (II) or a salt thereof can be prepared according to a similar method described in WO 95/17393, below-mentioned Preparations, and the like.

In the above and subsequent descriptions of the present specification, suitable examples and illustrations of the various definitions which the present invention includes within the scope thereof are explained in detail as follows.

Suitable "aryl" and aryl moiety in the terms "ar(lower)alkyl", "aryloxy", "ar(lower)alkenyl", "arylsulfonyl", "ar(lower)arylsulfonyl", "ar(lower)alkylsulfonyl", and "aryl oxysulfonyl" may include phenyl, lower alkylphenyl (e.g., tolyl, ethylphenyl, propylphenyl, etc.), naphthyl or the like.

Suitable "halogen" may include fluorine, chlorine, bromine, or iodine.

The term "lower" is intended to mean 1 to 6 carbon atom(s), unless otherwise indicated.

Suitable "lower alkyl" and lower alkyl moiety in the terms "lower alkylamino", "ar(lower)alkyl", "carboxy(lower)alkyl", "hydroxy(lower)alkyl", "ar(lower)alkylsulfonyl", and lower alkylsulfonyl may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "lower alkylamino" may include mono- or di-(lower)alkylamino, such as methylamino, dimethylamino, ethylamino, diethylamino, or the like.

Suitable "lower alkoxy" and lower alkoxy moiety in the term "hydroxy(lower)alkoxy" may include methoxy, ethoxy propoxy, isopropoxy, butoxy, isobutoxy, t-butoxy, pentyloxy, t-pentyloxy, hexyloxy, or the like, preferably methoxy.

Suitable "heterocyclic group" may include saturated or unsaturated, monocyclic or polycyclic heterocyclic group containing at least one nitrogen atom. And especially preferable heterocyclic ring containing nitrogen may be ones such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, pyrimidinyl, pyrazinyl, dihydropyridazinyl, tetrahydropyridazinyl, triazolyl (e.g., 1H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.,;

saturated 3 to 8-membered heteromonocyclic group containing 1 to 4 nitrogen atom(s), for example, pyrrolidinyl, imidazolidinyl, piperidinyl, piperazinyl, azacycloheptyl, azacyclooctyl, perhydroazepinyl, etc.,;

unsaturated condensed heterocyclic group containing 1 to 5 nitrogen atom(s), for example, indolyl, 2,3-dihydroindolyl, isoindolyl, indolinyl, indazolyl, isoindolinyl, indolizinyl, benzimidazolyl, quinolyl, 1,2,3,4-tetrahydroquinolyl, isoquinolyl, indazolyl, benzotriazolyl, tetrazolopyridyl, tetrazolopyridazinyl (e.g., tetrazolo[1,5-b]pyridazinyl,etc.,), dihydrotriazolopyridazinyl, etc.,;

unsaturated 3 to 8-membered heteromonocyclic group containing 1 to 2 oxygen atom(s) and 1 to 3 nitrogen atom(s), for example, oxazolyl, isoxazolyl, dihydroisoxazolyl, oxadiazolyl (e.g., 1,2,4-oxadiazolyl, 1,3,4-oxadiazolyl, 2,5-oxadiazolyl, etc.,), etc., saturated 3 to 8-membered heteromonocyclic group containing 1 to 2 oxygen atom(s) and 1 to 3 nitrogen atom(s), for example, morpholino, etc.,;

unsaturated condensed heterocyclic group containing 1 to 2 oxygen atom(s) and 1 to 3 nitrogen atom(s), for example, benzoxazolyl, benzoxadiazolyl, etc.,;

unsaturated 3 to 8-membered heteromonocyclic group containing 1 to 2 sulfur atom(s), for example, thienyl, thiepinyl, etc.,;

unsaturated 3 to 8-membered heteromonocyclic group containing 1 to 2 sulfur atom(s) and 1 to 3 nitrogen atom(s), for example, thiazolyl, isothiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.,;

saturated 3 to 8-membered heteromonocyclic group containing 1 to 2 sulfur atom(s) and 1 to 3 nitrogen atom(s), for example, thiazolidinyl, etc.,;

unsaturated condensed heteromonocyclic group containing 1 to 2 sulfur atom(s) and 1 to 3 nitrogen atom(s), for example, benzothiazolyl, benzothiadiazolyl, etc., and the like.

Suitable acyl and acyl moiety in the terms of "acylamino" and "acyloxy" may include aliphatic acyl group and acyl group containing an aromatic or heterocyclic ring.

And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkenoyl (e.g., propionyl, 2-methylpropionyl, butenoyl, or the like, preferably one having 3 to 4 carbon atom(s)); aroyl (benzoyl, naphthoyl, etc.); lower alkoxyaroyl (methoxyphenylcarbonyl, ethoxyphenylcarbonyl, propoxyphenylcarbonyl, isopropoxyphenylcabonyl, methoxynaphthylcarbonyl, ethoxynaphthylcarbonyl, propoxynaphtylcarbonyl, isopropoxynaphthyl-carbonyl, etc.); heterocyclic carbonyl ("heterocyclic moiety" in the term "heterocyclic carbonyl" can be referred above); bridged cyclic(lower)alkanecarbonyl (bicyclo[2.2.1]hept-2-yl-carbonyl, bicyclo[3.2.1]oct-2-yl-carbonyl, bicyclo[3.2.2]non-2-yl-carbonyl, bicyclo[3.2.2]non-3-yl-carbonyl, bicyclo[4.3.2]undec-2-yl-carbonyl, bicyclo[4.3.2]undec-3-yl-carbonyl, bicyclo[2.2.2)oct-2-en-2-yl-carbonyl, bicyclo3.2.2]non-3-en-3-yl-carbonyl, tricyclo[5.3.1.1]dodec-2-yl-carbonyl, tricyclo[5.3.1.1]dodec-3-yl-carbonyl, adamantylcarbonyl, etc.); cyclo(lower)-alkanecarbonyl (cyclopropanecarbonyl, cyclobutanecarbonyl, cyclopentanecarbonyl, cyclohexanecarbonyl, etc.), carbamoyl which may be substituted with mono- or di-(lower)alkyl (e.g. dimethylcarbamoyl, etc.) and the like.

Suitable "cyclo(lower)alkyl" may include cyclopropyl, cyclopentyl, cyclobutyl, cyclohexyl, or the like.

Suitable "cyclo(lower)alkenyl" may include cyclopentenyl, cyclohexenyl, cycloheptenyl, cyclooctenyl, cyclononenyl, or the like.

Suitable "protected carboxy" may include carboxylate, esterified carboxy, or the like.

Suitable example of the ester moiety of an esterified carboxy may be the ones such as lower alkyl (e.g., methyl, ethyl, propyl, isopropyl, butyl, isobutyl, tert-butyl, pentyl, hexyl, etc.) which may have at least one suitable substituent(s), for example, lower alkanoyloxy(lower)alkyl [e.g., acetoxymethyl, butyryloxymethyl, valeryloxymethyl, pivaloyloxymethyl, etc.], halo(lower)alkyl (e.g., 2-iodoethyl, 2,2,2-trichloroethyl, etc.); lower alkenyl (e.g., vinyl, allyl, etc.); lower alkynyl (e.g., ethynyl, propynyl, etc.); ar(lower)alkyl which may have at least one suitable substituent(s) (e.g., benzyl, 4-methoxybenzyl, 4-nitrobenzyl, phenethyl, trityl, etc.); aryl which may have at least one suitable substituent(s) (e.g., phenyl, tolyl, 4-chlorophenyl, tert-butylphenyl, xylyl, mesityl, cumenyl, etc.); phthalidyl; or the like.

Suitable "lower alkylene" may include straight or branched one having 1 to 6 carbon atom(s), such as methylene, ethylene, trimethylene, tetramethylene, pentamethylene and hexamethylene, preferably one having 1 to 3 carbon atom(s), more preferably methylene.

Suitable "cyclo($C_3$–$C_9$)alkane" may include cyclopropane, cyclobutane, cyclopentane, cyclohexane, cycloheptane, cyclooctane, cyclononane, or the like, preferably one having 5 to 7 carbon atoms.

Suitable "cyclo($C_5$–$C_9$)alkene" may include cyclopentene, cyclohexene, cycloheptene, cyclooctene, cyclononene, or the like, preferably one having 5 to 7 carbon atoms.

Preferred embodiments of the oxazole compounds (I) are as follows
wherein
$R^1$ is aryl which may be substituted with halogen(s),
$R^2$ is aryl which may be substituted with halogen(s),
X is single bond,

or $SO_2$,
$R^3$ and $R^4$ are independently
(1) hydrogen;
(2) hydroxy;
(3) lower alkyl which may be substituted with one or more substituent(s) selected from the group consisting of:
　(a) hydroxy,
　(b) cyano,
　(c) lower alkoxy,
　(d) hydroxy(lower)alkoxy,
　(e) cyclo(lower)alkyl,
　(f) cyclo(lower)alkenyl,
　(g) amino,
　(h) lower alkylamino,
　(i) carbamoyl,
　(j) carboxy,
　(k) protected carboxy,
　(l) heterocyclic group optionally substituted with ar(lower)alkyl or oxo, and
　(m) aryl optionally substituted with
　　hydroxy,
　　carboxy,
　　protected carboxy,
　　carboxy(lower)alkyl, or
　　lower alkoxy which may be substituted with carboxy or protected carboxy;
(4) lower alkoxy which may be substituted with aryl(s);
(5) aryl which may be substituted with one or more substituent(s) selected from the group consisting of:
　(a) aryloxy,
　(b) acylamino, and
　(c) carbamoyl;
(6) cyclo(lower)alkyl which may be substituted with hydroxy(s);
(7) arylsulfonyl;
(8) ar(lower)alkylsulfonyl;
(9) lower alkylsulfonyl;
(10) aryloxysulfonyl;
(11) heterocyclic group which may be substituted with one or more substituent(s) selected from the group consisting of:
　(a) ar(lower)alkyl,
　(b) aryl,
　(c) protected carboxy,
　(d) lower alkyl, and
　(e) oxo;
(12) acyl which may be substituted with aryl; or
(13) carbamoyl which may be substituted with acyl, ar(lower)alkyl, or arylsulfonyl,
　(wherein X is

neither $R^3$ nor $R^4$ is hydrogen),
$R^3$ and $R^4$ may be linked together to form

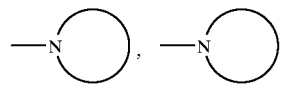

is N-containing heterocyclic group which may be substituted with one or more substituent(s) selected from the group consisting of:
(1) lower alkyl,
(2) aryl,
(3) protected carboxy,
(4) hydroxy(lower)alkyl,
(5) ar(lower)alkyl,
(6) hydroxy,
(7) oxo, and
(8) lower alkylamino,
$R^5$ is
(1) hydrogen,
(2) hydroxy,
(3) carboxy, or
(4) protected carboxy,
$A^1$ is lower alkylene or single bond,

is cyclo($C_3$–$C_9$)alkane or cyclo($C_5$–$C_9$)alkene,
or a pro-drug thereof, or a pharmaceutically acceptable salt thereof.

More preferred embodiments of the oxazole compounds (I) are as follows:

wherein
R$^1$ is aryl,
R$^2$ is aryl,
X is single bond $$\underset{O}{\overset{C}{\|}}$$

or SO$_2$,
R$^3$ and R$^4$ are independently
  (1) hydrogen;
  (2) hydroxy;
  (3) lower alkyl which may be substituted with one or more substituent(s) selected from the group consisting of:
    (a) hydroxy,
    (b) cyano,
    (c) lower alkoxy,
    (d) hydroxy(lower)alkoxy,
    (e) cyclo(lower)alkyl,
    (f) cyclo(lower)alkenyl,
    (g) amino,
    (h) lower alkylamino,
    (i) carbamoyl,
    (j) carboxy,
    (k) protected carboxy,
    (l) heterocyclic group optionally substituted with ar(lower)alkyl or oxo, and
    (m) aryl optionally substituted with
      hydroxy,
      carboxy,
      protected carboxy,
      carboxy(lower)alkyl, or
      lower alkoxy which may be substituted with carboxy or protected carboxy;
  (4) lower alkoxy which may be substituted with aryl(s);
  (5) aryl which may be substituted with one or more substituent(s) selected from the group consisting of:
    (a) aryloxy,
    (b) acylamino, and
    (c) carbamoyl;
  (6) cyclo(lower)alkyl which may be substituted with hydroxy(s);
  (7) arylsulfonyl;
  (8) ar(lower)alkylsulfonyl;
  (9) lower alkylsulfonyl;
  (10) aryloxysulfonyl;
  (11) heterocyclic group which may be substituted with one or more substituent(s) selected from the group consisting of:
    (a) ar(lower)alkyl,
    (b) aryl,
    (c) protected carboxy,
    (d) lower alkyl, and
    (e) oxo;
  (12) acyl which may be substituted with aryl; or
  (13) carbamoyl which may be substituted with acyl, ar(lower)alkyl, or arylsulfonyl,
    (wherein X is $$\underset{O}{\overset{C}{\|}},$$

neither R$^3$ nor R$^4$ is hydrogen),

R$^3$ and R$^4$ may be linked together to form

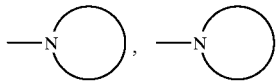

is N-containing heterocyclic group which may be substituted with one or more substituent(s) selected from the group consisting of:
  (1) lower alkyl,
  (2) aryl,
  (3) protected carboxy,
  (4) hydroxy(lower)alkyl,
  (5) ar(lower)alkyl,
  (6) hydroxy,
  (7) oxo, and
  (8) lower alkylamino,
R$^5$ is hydrogen,
A$^1$ is lower alkylene,

is
  (1) cyclohexane,
  (2) cyclohexene,
  (3) cyclopentane, or
  (4) cyclopentene,
or a pro-drug thereof, or a pharmaceutically acceptable salt thereof.

Furthermore preferred embodiments of the oxazole compounds (I) are as follows
wherein
R$^1$ is phenyl,
R$^2$ is phenyl,
X is $$\underset{O}{\overset{C}{\|}}$$

or SO$_2$,
R$^3$ and R$^4$ are independently
  (1) hydrogen;
  (2) lower alkyl which may be substituted with one or more substituent(s) selected from the group consisting of:
    (a) hydroxy,
    (b) heterocyclic group, and
    (c) phenyl;
  (3) lower alkoxy which may be substituted with phenyl; or
  (4) phenyl which may be substituted with phenyloxy;
    (wherein X is $$\underset{O}{\overset{C}{\|}},$$

neither R$^3$ nor R$^4$ is hydrogen), $R^3$ and $R^4$ are linked together to form

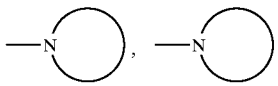

is N-containing heterocyclic group;
$R^5$ is hydrogen,
$A^1$ is methylene,

is
(1) cyclohexane,
(2) cyclohexene,
(3) cyclopentane, or
(4) cyclopentene,
or a pro-drug thereof, or a pharmaceutically acceptable salt thereof.

The most preferred embodiment of the oxazole compounds (I) is N-[(2-hydroxy-2-phenyl)ethyl]-3-{[(1S,2R)-2-(4,5-diphenyloxazol-2-yl)-1-cyclopentyl]methyl}benzamide, N-(2,2-diphenylethyl)-3-{[(1S,2R)-2-(4,5-diphenyl-oxazol-2-yl)-1-cyclopentyl]methyl}benzamide, N-benzyloxy-3-{[(1S)-2-(4,5-diphenyloxazol-2-yl)-2-cyclohexen-1-yl]methyl}benzamide or N-benzylsulfonyl-3-{[(1S)-2-(4,5-diphenyloxazol-2-yl)-2-cyclohexen-1-yl]methyl}benzamide.

The processes for preparing the object and starting compounds of the present invention are explained in detail in the following.

Process 1

The compound (IV) or a salt thereof can be prepared by reacting the compound (II) or a salt thereof, with the compound (III) or its reactive derivative at the amino group or a salt thereof.

Suitable reactive derivative of the compound (III) may include Schiff's base type amino or its tautomeric enamine type isomer formed by the reaction of the compound (III) with a carbonyl compound such as aldehyde, ketone or the like; a silyl derivative formed by the reaction of the compound (III) with a silylating reagent such as N,O-bis(trimethylsilyl)acetamide, N-trimethylsilylacetamide, or the like.

Suitable reactive derivative of the compound (II) may include an acid chloride, an acid anhydride, an activated amide, an activated ester, or the like.

Suitable acid anhydride may be a symmetric anhydride or a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfuric acid, thiosulfuric acid, alkanesulfonic acid (e.g., methanesulfonic acid, ethanesulfonic acid, etc.), alkylcarbonic acid, aliphatic carboxylic acid (e.g., pivalic acid, pentanoic acid, isopentanoic acid, etc.); aromatic carboxylic acid (e.g., benzoic acid, chlorobenzoic acid, fluorobenzoic acid, nitrobenzoic acid, etc.), or the like.

Suitable activated amide may be imidazolylamide, 4-substituted imidazolylamide, dimethylpyrazolylamide, triazolylamide, tetrazolylamide, or the like.

Suitable activated ester may be dimethyliminomethyl [$(CH_3)_2N^+$=CH—] ester, vinyl ester, propargyl ester, 4-nitrophenyl ester, 2,4-dinitrophenyl ester, trichlorophenyl ester, pentachlorophenyl ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an activated ester with a N-hydroxy compound (e.g., N,N-dimethylhydroxylamine, 1-hydroxy-2H-pyridone, N-hydroxysuccinimido, N-hydroxybenzotrioxazole, N-hydroxyphthalimide, etc.), or the like.

These reactive derivatives can optionally be selected from them according to the kind of compound (II) to be used.

When the compound (II) is used in free acid form or its salt form in the reaction, the reaction is preferably carried out in the presence of condensing agent.

Suitable condensing agent may include a carbodiimide (e.g., N,N'-dicyclohexylcarbodiimido, N-cyclohexyl-N'-(4-diethylaminocyclohexyl) carbodiimido, N-ethyl-N'-(3-dimethylaminopropyl)carbodiimido or its hydrochloride) diphenylphosphinic azido, diphenylphosphinic chloride, diethylphosphoryl cyanide, bis(2-oxo-3-oxazolidinyl) phosphinic chloride, N,N'-carbonyldiimidazole, 2-ethoxy-1-ethoxycarbonyl-1,2-dihydroquinoline, cyanuric chloride, or the like.

The reaction may be also carried out in the presence of organic or inorganic base such as alkali metal carbonate, tri(lower)alkylamine, pyridine, N-(lower)alkylmorphorine, or the like.

The reaction is usually carried out in a conventional solvent such as water, acetone, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

Suitable salts of the object compound (I) including the compounds (IV) and (V), and the compounds (II) and (V) are pharmaceutically acceptable conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, etc.), an organic acid salt (e.g., acetate, maleate, tartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), or the like.

Process 2

The compound (VI) or a salt thereof can be prepared by reacting the compound (V) or a salt thereof, with the compound (III) or its reactive derivative at the amino group or a salt thereof.

This reaction can be referred to that of Examples 6-1 and 6-2.

Process 3

The compound (IX) or a salt thereof can be prepared by reacting the compound (VII) or a salt thereof, with the compound (VIII) or its reactive derivative at the carboxy group or a salt thereof.

Suitable reactive derivative at the carboxy group may include its halide (carbonyl chloride, carbonyl bromide, etc.), its anhydride, its activated ester and the like.

This reaction can be referred to that of Examples 7-1 and 7-2.

Process 4

The compound (XI) or a salt thereof can be prepared by reacting the compound (VII) or a salt thereof, with the compound (X) or a salt thereof.

This reaction can be referred to that of Examples 7-3, 7-4 and 7-5.

Process 5

The compound (XIII) or a salt thereof can be prepared by reacting the compound (VII) or a salt thereof, with the compound (XII) or its reactive derivative at the sulfo group or a salt thereof.

Suitable reactive derivative at the sulfo group may include its halide (sulfonyl chloride, etc.), its anhydride, its activated ester and the like.

This reaction can be referred to that of Example 7-6.

$PGE_2$ is known as one of the metabolites in an arachidonate cascade. And it is also known that it has various activities such as pain inducing activity, inflammatory activity, uterine contractile activity, a promoting effect on digestive peristalsis, an awaking activity, a suppressive effect on gastric acid secretion, hypotensive activity, blood platelet inhibition activity, bone-resorbing activity, angiogenic activity, or the like.

$PGE_2$-sensitive receptors have been sub-divided into four subtypes, EP1, EP2, EP3 and EP4, and these receptors have a wide distribution in various tissues. The effects associated with EP1 receptor are believed to be mediated by mobilization of $Ca^{2+}$ from intracellular stores. The EP3 receptor is an example of promiscuous receptor that may couple to different second-messenger systems. Further, the effects associated with EP2 and EP4 receptors may be considered as inhibitory, and are in believed to be associated with a stimulation of adenyl cyclase and an increase in levels of intracellular cyclic AMP. Especially, EP4 receptor may be considered to be associated with smooth muscle relaxation, anti-inflammatory or pro-inflammatory activities, lymphocyte differentiation, antiallergic activities, mesangial cell relaxation or proliferation, gastric or enteric mucus secretion, or the like.

The oxazole compounds represented by the formula (I) or its salts thereof possess binding activities to $PGE_2$-sensitive receptors, specifically to EP4 receptor, therefore they possess a $PGE_2$-antagonizing or $PGE_2$-inhibiting activity.

Therefore, the compounds represented by the formula (1) or its salts thereof are useful for preventing or treating a $PGE_2$ mediated diseases, especially a EP4 receptors-mediated diseases, such as inflammatory conditions, various pains, or the like in human beings or animals.

More particularly, $PGE_2$ agonist or antagonist, such as the compounds represented by formula (I) and its salt thereof, are useful for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, or the like in human being or animal.

Furthermore particularly, $PGE_2$ antagonist (especially, EP4 receptor blocker) such as the compounds represented by formula (I) and its salt thereof are useful for treating or preventing mesangial proliferative glomerulonephritis.

Generally, nephritis is classified into two major categories: glomerulonephritis and interstitial nephritis. Among these, glomerulonephritis is additionally sub-classified as follows:

(1) minimal change;

(2) focal segmental glomerulosclerosis;

(3) membranous nephropathy;

(4) endocapillary proliferative glomerulonephritis;

(5) mesangial proliferative glomerulonephritis;

(6) membranoproliferative glomerulonephritis; and (7) crescentic glomerulonephritis.

The inventors of the present invention found that $PGE_2$ antagonist (especially EP4-receptor blocker) was effective for treating or preventing mesangial proliferative glomerulonephritis among the above-mentioned symptoms. Specifically, it is a new fact found by the inventors of the present invention that $PGE_2$ antagonist is effective for treating or preventing mesangial proliferative glomerulonephritis. The inventors of the present invention have confirmed that one of $PGE_2$ antagonist, namely, the compound of this invention, is effective for treating or preventing mesangial proliferative glomerulonephritis, as evidenced below in Experiment Data.

The compound represented by the formula (I) or its salts thereof are also useful for the preparation of medicament having diuretic activity, which arc useful for the preparation of drugs indicated treating or preventing various edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like.

In order to show the utility of the object compound (I), pharmacological data of the representative compounds thereof are shown in the following.

Binding Assay Using Expression of Prostanoide Receptor Subtype

[I] Test Compound (1) N-[(2-hydroxy-2-phenyl)ethyl]-3-{[(1S,2R)-2-(4,5-diphenyloxazol-2-yl)-1-cyclopentyl]methyl}benzamide Example 1-47

(2) N-(2,2-diphenylethyl)-3-{[(1S,2R)-2-(4,5-diphenyloxazol-2-yl)-1-cyclopentyl]methyl}benzamide Example 1-50

(3) N-benzyloxy-3-{[(1S)-2-(4,5-diphenyloxazol-2-yl)-2-cyclohexen-1-yl]methyl}benzamide Example 2-46

(4) N-benzylsulfonyl-3-{[(1S)-2-(4,5-diphenyloxazol-2-yl)-2-cyclohexen-1-yl]methyl}benzamide Example 2-75

[II] Test Method

The membrane fraction was prepared using COS-7 cells transfected prostanoide receptor subtype (human EP4).

The standard assay mixture contained membrane fraction, [$^3$H]-PGE$_2$ in final volume of 0.25 ml was incubated for 1 hour at 30° C. The reaction was terminated by that the mixture was rapidly filtered through a glass filter (GF/B). Then the filter was washed by 4ml of ice-cold buffer at two times. The radioactivity associated with the filter was measured by liquid scintillation counting.

In the experiment for competition of specific [$^3$H]-PGE$_2$ was added at a concentration of 10 $\mu$M. The following buffer was used in all reactions.

Buffer: 20 mM Mes (pH 6.0), 1 mM EDTA, 10 mM MgCl$_2$

The inhibition (%) of each compound at a concentration of 10 $\mu$M was shown in Table.

[III] Test Result

| Test Compound (1.0 × 10$^{-7}$M) | Inhibition (%) |
|---|---|
| (1) | ≧80 |
| (2) | ≧80 |
| (3) | ≧80 |
| (4) | ≧80 |

Methods of Mesangial Proliferative Glomerulonephritis Model

Female Wistar rats, 6 weeks old were purchased from SLC (Shizuoka, Japan). Glomerulosclerosis model was produced by intravenous injections (i.v.) of the monoclonal antibody (mAb), MRC OX-7 (Dainippon Co. Ltd., Osaka, Japan). The 8 weeks old rats were divided into 4 groups (10 rats/group). Group 1 was injected saline instead of OX-7 as a normal group and treated with vehicle (0.5% methylcellulose solution) only. Group 2 was also treated with the vehicle only after the injection of 1 mg/kg OX-7 as a control group. Group 3 and Group 4 were treated with N-benzylsulfonyl-3-{[(1S)-2-(4,5-diphenyloxazol-2-yl)-2-cyclohexen-1-yl]methyl}benzamide (Example 2-75), as shown in the following Table. The compound was orally given every day from 5 days before to one day after i.v. administration of the antibody. Urine was collected for 24 hours from the rats in metabolic cages 1 day after injection of OX-7 and the amount of protein in each sample was determined by the biuret method using bovine serum albumine as the standard. All the rats were sacrificed 2 days after injection of OX-7. Blood biochemical analysis was carried out.

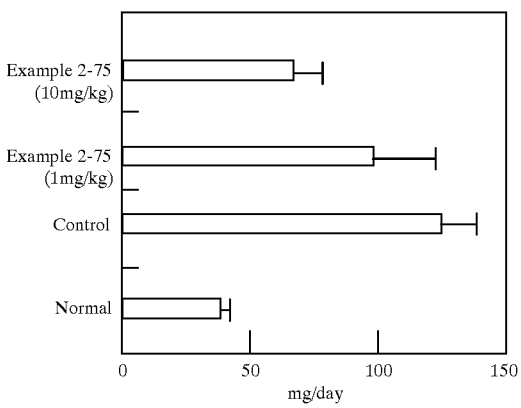

| Group | Urinary Protein (mg/day) |
|---|---|
| Normal | 40.8 ± 2.3 |
| Control | 127.9 ± 12.6 |
| Example 2-75 (1 mg/kg) | 98.2 ± 20.9 |
| Example 2-75 (10 mg/kg) | 66.4 ± 6.9 |

The pharmaceutical composition of the present invention can be used in the form of a pharmaceutical preparation, for example, in solid, semisolid or liquid form (e.g., tablet, pellet, troche, capsule, suppository, cream, ointment, aerosol, powder, solution, emulsion, suspension etc.), which contains the object compound (1) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyloneglycol, sucrose, starch, etc.), disintegrator (e.g., starch, carboxymethyl cellulose, calcium salt of carboxymethyl cellulose, hydroxypropylstarch, sodium glycol-starch, sodium bicarbonate, calcium phosphate, calcium citrate, etc.), lubricant (e.g., magnesium stearate, talc, sodium laurylsulfate, etc.), flavoring agent (e.g., citric acid, mentol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water), base wax (e.g., cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The patents, patent applications and publications cited herein are incorporated by referance.

Abbreviations used in this application are as follows:
EtOAc: Ethyl acetate
DMF: N,N-Dimethylformamide
MeOH: Methyl alcohol
NMP: N-Methylpyrrolidinone
DMSO: Dimethylsulfoxide The following Preparations and Examples are given only for the purpose of illustrating the present invention in more detail.

Preparation 1

To a solution of 1-cyclohexene-1-carboxylic acid (100 g) in methylene chloride (800 ml) was added sulfinyl chloride (117 ml) at room temperature. After stirring the mixture for 4 hours, the solvent was evaporated in vacuo. The residue was diluted with methylene chloride (IL) and benzoin (170 g) and triethylamine (166 ml), and dimethylaminopyridine (10 g) were added to the solution at 0° C. under $N_2$. After stirring the mixture for 4 hours at room temperature, the solvent was evaporated in vacuo, and the residue was partitioned between EtOAc and water. The organic layer was washed with 1N-hydrochloric acid solution, saturated sodium hydrogencarbonate, and brine, dried over magnesium sulfate, and evaporated in vacuo. The obtained compound and ammonium acetate (200 g) were dissolved in acetic acid (1500 ml) and the mixture was stirred for 4 hours at 100° C. After the solvent was removed, the residue was partitioned between EtOAc and water. The organic layer was washed with water, saturated sodium hydrogencarbonate and brine. The dried solvent was evaporated in vacuo and the residue was purified by chromatography on silica gel to give 1-(4,5-diphenyloxazol-2-yl)-1-cyclohexene (171 g).

$^1$H-NMR (CDCl$_3$, δ): 1.6–1.9 (4H, m), 2.2–2.4 (2H, m), 2.5–2.7 (2H, m), 6.90 (1H, m), 7.2–7.8 (10H, m)

MS (m/z): 302(M+H)$^+$

Preparation 2

A solution of AD-mix-α (30 g) in a mixture of t-butanol (600 ml) and water (600 ml) was stirred for 1 hour, and then methanesulfonamide (9.3 g) and 1-(4,5-diphenyloxazol-2-yl)-1-cyclohexene added to the solution at room temperature. After stirring the mixture for 20 hours at the same temperature, sodium sulfite (60 g) was added, and the mixture was stirred for 30 minutes. The mixture was partitioned between EtOAc and water. The organic layer was washed with 1N-hydrochloric acid solution, saturated sodium hydrogencarbonate and brine, dried over magnesium sulfate and evaporated in vacuo. The residue was purified by chromatography on silica gel to afford (1R,2S)-1,2-dihydroxy-1-(4,5-diphenyloxazol-2-yl)cyclohexane (30 g).

IR (neat, cm$^{-1}$): 3400, 3200, 1460

$^1$H-NMR (CDCl$_3$, δ): 1.2–1.9 (7H, m), 2.2–2.4 (1H, m), 3.34 (1H, s), 3.70 (1H, br s), 4.1–4.4 (1H, m), 7.2–7.8 (10H, m)

MS (m/z): 365 (M+H)$^+$

Preparation 3

To a solution of (1R,2S)-1,2-dihydroxy-1-(4,5-diphenyloxazol-2-yl)cyclohexane (18 g) in methylene chloride (200 ml) were added orthoacetic acid trimethyl ester (9.7 ml) and p-toluenesulfonic acid (20 mg) at room temperature under $N_2$. After stirring the mixture for 30 minutes, the solvent was evaporated in vacuo. The residue was diluted with methylene chloride (200 ml) and acetyl bromide (5.8 ml) was added to the solution at 0° C. under $N_2$. After stirring the mixture for 2 hours at room temperature, the solvent was evaporated in vacuo, the residue was diluted with MeOH (200 ml), and potassium carbonate (12 g) was added to the solution at room temperature. The mixture was stirred for 2 hours at the same temperature and partitioned between EtOAc and water. The organic layer was washed with 1N-hydrochloric acid, water, saturated sodium hydrogencarbonate and brine. The dried solvent was evaporated in vacuo and the residue was purified by chromatography on silica gel to give (1R,2S)-1-(4,5-diphenyloxazol-2-yl)-1,2-epoxycyclohexane (14.1 g).

$^1$H-NMR (CDCl$_3$, δ): 1.2–1.8 (4H, m), 1.9–2.2 (2H, m), 2.2–2.4 (1H, m), 2.6–2.8 (1H, m), 3.83 (1H, m), 7.2–7.6 (10H, m)

MS (m/z): 318 (M+H)$^+$

Preparation 4

To a solution of (1R,2S)-1-(4,5-diphenyloxazol-2-yl)-1,2-epoxycyclohexane (20 g) and copper bromide (3.0 g) in tetrahydrofuran (400 ml) was dropwise added a solution of 3-methoxybenzylmagnesium chloride [prepared from 3-methoxybenzylchloride (50 g) and Mg (9.2 g)] in tetrahydrofuran (500 ml) at −78° C. under $N_2$. The mixture was stirred for 2 hours at the room temperature and partitioned between EtoAc and water. The organic layer was washed with 1N-hydrochloric acid, water, saturated sodium hydrogencarbonate and brine. The dried solvent was evaporated in vacuo and the residue was purified by chromatography on silica gel to give (1R,2S)-1-(4,5-diphenyloxazol-2-yl)-1-hydroxy-2-(3-methoxybenzyl)cyclohexane (29.2 g).

IR (Nujol, cm$^{-1}$): 3400, 1600

$^1$H-NMR (CDCl$_3$, δ): 1.4–2.4 (9H, m), 3.07 (1H, d, J=10 Hz), 3.52 (1H, m), 3.74 (3H, s), 6.7–6.9 (4H, m), 7.15 (1H, t, J=8 Hz), 7.2–7.8 (10H, m)

MS (m/z): 440 (M+H)$^+$

Preparation 5

A mixture of (1R,2S)-1-(4,5-diphenyloxazol-2-yl)-1-hydroxy-2-(3-methoxybenzyl)cyclohexane (28 g) and p-toluene-sulfonic acid (2.5 g) in toluene (300 ml) was stirred for 4 hours under reflux. The solution was washed with water, saturated sodium hydrogencarbonate and brine, dried over magnesium sulfate and evaporated in vacuo. The residue was purified by chromatography on silica gel to afford (S)-2-(4,5-diphenyloxazol-2-yl)-1-(3-methoxybenzyl)-2-cyclohexene (16 g).

Hu 1H-NMR (CDCl$_3$, δ): 1.4–1.9 (4H, m), 2.1–2.4 (2H, m), 2.53 (1H, dd, J=10.2, 12.8 Hz), 3.1–3.3 (1H, m), 3.31 (1H, dd, J=3.2, 12.8 Hz), 3.77 (3H, s), 6.80 (1H, 8 Hz), 6.9–7.0 (3H, m), 7.20 (1H, t, J=8 Hz), 7.2–7.8 (10 H, m)

MS (m/z): 422 (M+H)$^+$

Preparation 6

To a solution of (S)-2-(4,5-diphenyloxazol-2-yl)-1-(3-methoxybenzyl)-2-cyclohexene (8.5 g) in methylene chloride (100 ml) was added boron tribromide (50ml, 1M solution in methylene chloride) at 0° C. After stirring the mixture for 2 hours, the solvent was evaporated in vacuo. The residue was diluted with EtOAc, and the mixture was washed with water and brine. The dried solvent was evaporated in vacuo and dissolved in methylene chloride (50 ml). To the solution were added trifluoromethanesulfonic acid anhydride (5.0 ml) and 2,6-lutidine (6.2 ml) at −78° C. After stirring the mixture for 2 hours, the solvent was evaporated in vacuo. The residue was diluted with EtOAc, and the mixture was washed with water, saturated sodium hydrogencarbonate and brine. The dried solvent was evaporated in vacuo and the residue was purified by chromatography on silica gel to give (S)-3-{[2-(4,5-diphenyloxazol-2-yl)-2-cyclohexen-1-yl]methyl}phenyltrifluoromethanesulfonate (9.1 g).

IR (Nujol, cm$^{-1}$): 1600, 1520, 1480

¹H-NMR (CDCl₃, δ) 1.4–2.0 (4H, m), 2.2–2.4 (2H, m), 2.60 (1H, dd, J=10.4, 13.2 Hz), 3.0–3.2 (1H, m), 3.35 (1H, dd, J=4.0, 13.2 Hz), 6.9 (1H, m), 7.1–7.8 (14H, m)

MS (m/z): 540 (M+H)⁺

Preparation 7

To a solution of (S)-3-{[2-(4,5-diphenyloxazol-2-yl)-2-cyclohexen-1-yl]methyl}phenyl trifluoromethanesulfonate (7 g) in a mixture of MeOH (30 ml) and DMF (40 ml) were added 1,3-bis(diphenylphosphino)propane (1.1 mg), palladium acetate (0.58 mg), and triethylamine (5.4 ml). After stirring the mixture for 5 hours at 80° C. under CO atmosphere, the resultant mixture was partitioned between EtOAc and water and the organic layer was washed with 1N-hydrochloric acid, saturated sodium hydrogencarbonate, and brine. The dried solvent was evaporated in vacuo and the obtained solid was washed with ether to afford methyl (S)-3-{[2-(4,5-diphenyloxazol-2-yl)-2-cyclohexen-1-yl] methyl}benzoate (4.2 g).

IR (Nujol, cm⁻¹): 1720

¹H-NMR (CDCl₃, δ) 1.4–2.0 (4H, m), 2.1–2.4 (2H, m), 2.62 (1H, dd, J=10.0, 13.0 Hz), 3.16 (1H, m), 3.33 (1H, dd, J=3.0, 13.0 Hz), 3.88 (3H, s), 6.92 (1H, t, J=4.0 Hz), 7.3–7.8 (12H, m), 7.85 (1H, d, J=8 Hz), 8.00 (1H, s)

MS (m/z): 450 (M+H)⁺

Preparation 8

To a solution of methyl (S)-3-{[2-(4,5-diphenyloxazol-2-yl)-2-cyclohexen-1-yl]methyl}benzoate (0.3 g) in a mixture of ethanol (8 ml) and tetrahydrofuran (5 ml) was added 1N-sodium hydroxide solution (3.5 ml). After stirring the mixture for 24 hours at the same temperature, the solvent was removed. The residue was partitioned between EtOAc and 1N-hydrochloric acid, and the organic layer was washed with brine. The dried solvent was evaporated in vacuo and the obtained solid was washed with a mixture hexane and ether to afford (S)-3-{[2-(4,5-diphenyl-oxazol-2-yl)-2-cyclohexen-1-yl]methyl}benzoic acid (0.28 g).

IR (Nujol, cm⁻¹): 1700

¹H-NMR (CDCl₃, δ): 1.4–1.9 (4H, m), 2.2–2.4 (2H, m), 2.65 (1H, dd, J=10.0, 13.0 Hz), 3.2 (1H, m), 3.35 (1H, dd, J=3.0, 13.0 Hz), 6.93 (1H, t, J=3.8 Hz), 7.2–7.8 (12H, m), 7.93 (1H, d, J=8 Hz), 8.10 (1H, s)

MS (m/z): 436 (M+H)⁺

Preparation 9

The following compounds described in (1) to (3) were prepared according to a similar manner to those of Preparations 6, 7 and 8.

(1) 3-{[(1S,2R)-2-(4,5-diphenyloxazol-2-yl)-1-cyclopentyl]-methyl}benzoic acid

IR (Nujol, cm⁻¹): 1680

¹H-NMR (CDCl₃, δ): 1.4–2.5 (6H, m), 2.5–3.1 (4H, m), 7.2–7.8 (12H, m), 7.82 (1H, d, J=8 Hz), 7.93 (1H, S)

MS (m/z): 424 (M+H)⁺

(2) 3-{[(1SR,2RS)-2-(4,5-diphenyloxazol-2-yl)-1-cyclopentyl]methyl}benzoic acid

¹H-NMR (CDCl₃, δ) 1.4–2.5 (6H, m), 2.5–3.1 (4H, m), 7.2–7.8 (12H, m), 7.82 (1H, d, J=8 Hz), 7.93 (1H, S)

MS (m/z): 424 (M+H)

(3) 3-{[2-(4,5-diphenyloxazol-2-yl)-2-cyclohexen-1-yl]-methyl}benzoic acid

¹H-NMR (CDCl₃, δ): 1.4–1.9 (4H, m), 2.2–2.4 (2H, m), 2.65 (1H, dd, J=10.0, 13.0 Hz), 3.2 (1H, m), 3.35 (1H, dd, J=3.0, 13.0 Hz), 6.93 (1H, t, J=3.8 Hz), 7.2–7.8 (12H, m), 7.93 (1H, d, J=8 Hz), 8.10 (1H, s)

MS (m/z): 436 (M+H)⁺

EXAMPLES 1-1 TO 1-71

The following compound (Ia) was obtained according to the following Examples 1-1 to 1-71.

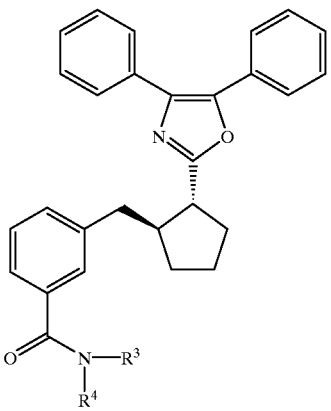

(Ia)

wherein R³ and R⁴ are as defined as the following Table 1.

Concerning each Example, the formula

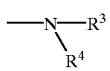

in the compound (Ia) and its MS spectrum were shown in Table 1.

TABLE 1

| Example No. | —N(R³)(R⁴) | MS (m/z) |
|---|---|---|
| 1-1 | cyclohexyl-N(CH₃)– | 519 (M + H)⁺ |
| 1-2 | CH₃-NH-CH₂CH₂CH₂-N(pyrrolidine) | 534 (M + H)⁺ |
| 1-3 | cyclohexyl-NH-CH₃ | 505 (M + H)⁺ |
| 1-4 | CH₃-N(CH₂CH₂OH)– | 481 (M + H)⁺ |
| 1-5 | CH₃-NH-(1-benzylpiperidin-4-yl) | 596 (M + H)⁺ |

TABLE 1-continued

| Example No. | –N(R³)(R⁴) | MS (m/z) |
|---|---|---|
| 1-6 | N-methylpiperazine-N'-COOC₂H₅ | 564 (M + H)⁺ |
| 1-7 | N-methyl-N'-phenylpiperazine | 568 (M + H)⁺ |
| 1-8 | N-methylpiperidine | 491 (M + H)⁺ |
| 1-9 | N-methyl-diphenylmethylamine | 589 (M + H)⁺ |
| 1-10 | N-methylbenzylamine | 513 (M + H)⁺ |
| 1-11 | N-methyl-n-propylamine (CH₃NHCH₂CH₂CH₃) | 479 (M + H)⁺ |
| 1-12 | N-methylcyclopropylamine | 463 (M + H)⁺ |
| 1-13 | N-methylethanolamine | 467 (M + H)⁺ |
| 1-14 | N-methyl-2-methoxyethylamine | 481 (M + H)⁺ |
| 1-15 | CH₃NHCH₂CH₂OCH₂CH₂OH | 511 (M + H)⁺ |
| 1-16 | (S)-1-methyl-3-(methylamino)pyrrolidine | 506 (M + H)⁺ |
| 1-17 | (R)-3-(methylamino)pyrrolidine (N-CH₃) | 506 (M + H)⁺ |
| 1-18 | N-methylaniline | 499 (M + H)⁺ |
| 1-19 | (S)-1-methyl-2-(hydroxymethyl)pyrrolidine | 507 (M + H)⁺ |
| 1-20 | 1-ethyl-3-(methylamino)piperidine | 534 (M + H)⁺ |
| 1-21 | 1-methylindoline | 525 (M + H)⁺ |
| 1-22 | 1,4-dimethylpiperazine | 506 (M + H)⁺ |
| 1-23 | 3-(methylamino)-ε-caprolactam | 534 (M + H)⁺ |
| 1-24 | 1-methyl-4-hydroxypiperidine | 507 (M + H)⁺ |
| 1-25 | 2-methyl-1,2,3,4-tetrahydroisoquinoline | 539 (M + H)⁺ |
| 1-26 | 1-methyl-4-benzylpiperidine | 591 (M + H)⁺ |
| 1-27 | 1-methyl-4-piperidinone | 505 (M + H)⁺ |

TABLE 1-continued

| Example No. | —N(R³)(R⁴) | MS (m/z) |
|---|---|---|
| 1-28 | N-methyl-N-butyl-benzylamine group (N-CH₂-Ph, N-CH₃, (CH₂)₃CH₃) | 569 (M + H)⁺ |
| 1-29 | 3-(methylamino)pyridine | 500 (M + H)⁺ |
| 1-30 | CH₃NH-CH₂-C(CH₃)₂-NH₂ | 494 (M + H)⁺ |
| 1-31 | 4-phenoxyphenyl-NHCH₃ | 591 (M + H)⁺ |
| 1-32 | 6-(methylamino)-1H-indazole | 539 (M + H)⁺ |
| 1-33 | 3-acetamido-phenyl-NHCH₃ | 556 (M + H)⁺ |
| 1-34 | (CH₃)₂N-CH₂CH₂-N(CH₃)- | 508 (M + H)⁺ |
| 1-35 | 4-carbamoyl-phenyl-NHCH₃ | 542 (M + H)⁺ |
| 1-36 | trans-4-hydroxycyclohexyl-NHCH₃ | 521 (M + H)⁺ |
| 1-37 | (CH₃)₂N-CH₃ | 451 (M + H)⁺ |
| 1-38 | CH₃NH-CH₂-CONH₂ | 480 (M + H)⁺ |
| 1-39 | PhCH₂CH₂-N(CH₃)₂ | 541 (M + H)⁺ |
| 1-40 | Ph-CH(OH)-CH₂-N(CH₃)- | 557 (M + H)⁺ |
| 1-41 | CH₃NH-CH₂-CH(OH)-CH₃ | 481 (M + H)⁺ |
| 1-42 | CH₃NH-CH(CH₃)-CH₂OH | 481 (M + H)⁺ |
| 1-43 | CH₃NH-CH₂CH₂CH₂-OH | 481 (M + H)⁺ |
| 1-44 | (CH₃)₂N-OH | 453 (M + H)⁺ |
| 1-45 | Ph-CH₂CH₂-NHCH₃ | 527 (M + H)⁺ |
| 1-46 | Ph-CH₂CH₂CH₂-NHCH₃ | 541 (M + H)⁺ |
| 1-47 | Ph-CH(OH)-CH₂-NHCH₃ | 543 (M + H)⁺ |
| 1-48 | Ph-CH₂-CH(NHCH₃)-CH₂OH | 557 (M + H)⁺ |

TABLE 1-continued
| Example No. | —N(R³)(R⁴) | MS (m/z) |
|---|---|---|
| 1-49 | 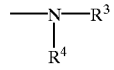 N-methylmorpholine | 493 (M + H)⁺ |
| 1-50 | 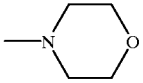 | 603 (M + H)⁺ |
| 1-51 | 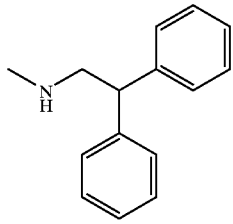 | 507 (M + H)⁺ |
| 1-52 | 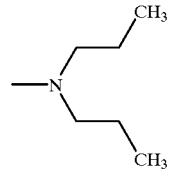 | 529 (M + H)⁺ |
| 1-53 | 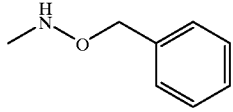 | 591 (M + H)⁺ |
| 1-54 | 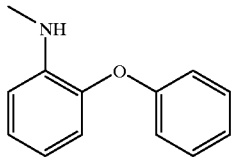 | 542 (M + H)⁺ |
| 1-55 | 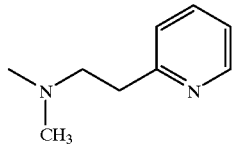 | 563 (M + H)⁺ |
| 1-56 | 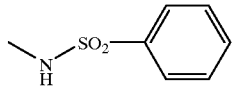 | 597 (M + H)⁺ |
| 1-57 | 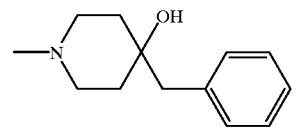 | 494 (M + H)⁺ |
| 1-58 | 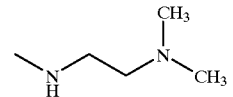 | 555 (M + H)⁺ |
| 1-59 | 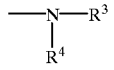 | 603 (M + H)⁺ |
| 1-60 | 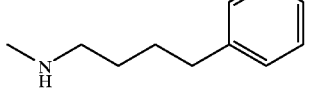 | 528 (M + H)⁺ |
| 1-61 | 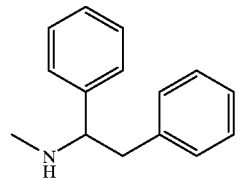 | 528 (M + H)⁺ |
| 1-62 |  | 528 (M + H)⁺ |
| 1-63 | 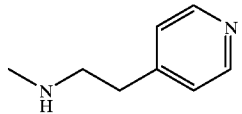 | 493 (M + H)⁺ |
| 1-64 |  | 533 (M + H)⁺ |
| 1-65 | 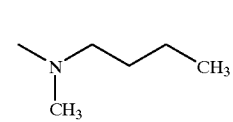 | 566 (M + H)⁺ |
| 1-66 |  | 535 (M + H)⁺ |
| 1-67 | 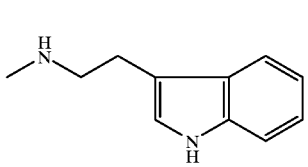 | 493 (M + H)⁺ |

TABLE 1-continued

| Example No. | —N—R³ \| R⁴ | MS (m/z) |
|---|---|---|
| 1-68 | 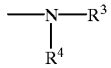 | 531 (M + H)⁺ |
| 1-69 | 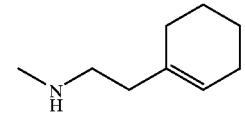 | 592 (M + H)⁺ |
| 1-70 | 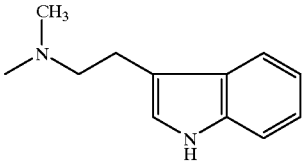 | 439 (M + H)⁺ |
| 1-71 | 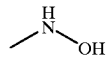 | 453 (M + H)⁺ |
| 1-72 | 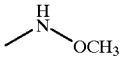 | 543 (M + H)⁺ |

EXAMPLES 1-1 TO 1-44 AND 1-56 TO 1-71

Coupling of 3-{[(1SR,2RS)-2-(4,5-diphenyloxazol-2-yl)-1-cyclopentyl]methyl}benzoic acid with n different type of amines (n=60)

To a solution of 3-{[(1SR,2RS)-2-(4,5-diphenyloxazol-2-yl)-1-cyclopentyl]methyl}benzoic acid (n×0.01 mmol) and 2-(1H-benzotrioxazol-1-yl)-1,1,3,3-tetramethyluronium tetrafluoroborate (TBTU) (n×0.015 mmol) in DMF (n×20 μl) was added a 1M DMF solution of diisopropylethylamine (n×14 μl), and the mixture was stirred at 27–30° C. for 1 hour. This activated acid solution was then distributed equally into n reaction vessels and to each reaction vessel was added 1M DMF or NMP solution of an amine [14 μl, n different type of amines (n=60)] and stirred at 27–30° C. for 2 hours.

To each reaction mixture was added 5% sodium hydrogencarbonate solution (0.40 ml), following by extraction with EtOAc (0.35 ml). The resultant aqueous layer was further extracted with EtOAc (0.20 ml×2). The combined organic layer was washed with water (0.30 ml). Then the resultant aqueous layer was additionally extracted with EtOAc (0.20 ml×2). The combined organic layer was concentrated by nitrogen flow and the resultant residue was dissolved in DMSO (1.0 ml) to give a ca. $10^{-2}$M DMSO solution of the above compound (Ia) which was subjected to analysis by MS spectrum.

EXAMPLE 1-45

To a mixture of 3-{[(1S,2R)-2-(4,5-diphenyloxazol-2-yl)-1-cyclopentyl]methyl}benzoic acid (140 mg, 0.331 mmol) and 2-phenylethylamine (0.046 ml, 0.364 mmol) in DMF (5 ml) was added 1-hydroxybenzotrioxazole (49 mg, 0.364 mmol) and 1-ethyl-3-(3'-dimethylaminopropyl) carbodiimide hydrochloride (95 mg, 0.495 mmol). After stirring the mixture at room temperature for 2.5 hours, the reaction mixture was diluted with EtOAc (30 ml), washed with water, saturated sodium hydrogencarbonate solution, water, and brine. The resultant mixture was dried over magnesium sulfate, and evaporated in vacuo. The resultant residue was purified by silica gel column chromatography (hexane:EtOAc, 2:1 elution) to give N-(2-phenylethyl)-3-{[(1S,2R)-2-(4,5-diphenyloxazol-2-yl)-1-cyclopentyl]methyl}benzamide (172.1 mg, 99%).

IR (KBr, cm⁻¹): 3307, 3059, 3026, 2941, 2870, 1639, 1533, 1446, 1300

¹H-NMR (CDCl₃, δ): 1.35–1.55 (1H, m), 1.67–2.30 (6H, m), 2.50–3.05 (6H, m), 3.35–3.65 (2H, m), 5.94–6.08 (1H, m), 7.13–7.62 (19H, m)

MS (m/z): 527 (M+H)⁺

EXAMPLE 1-46

The following compound was obtained in a similar manner to that of Example 1-45.

N-(3-phenylpropyl)-3-{[(1S,2R)-2-(4,5-diphenyloxazol-2-yl)-1-cyclopentyl]methyl}benzamide IR (KBr, cm⁻¹): 3307, 3057, 3026, 2937, 2866, 1637, 1535, 1444, 1298

¹H-NMR (CDCl₃, δ): 1.35–1.55 (1H, m), 1.68–2.30 (7H, m), 2.57–3.40 (8H, m), 5.93–6.08 (1H, m), 7.13–7.60 (19H, m)

MS (m/z) : 541 (M+H)⁺

EXAMPLE 1-47

The following compound was obtained in a similar manner to that of Example 1-45.

N-[(2-hydroxy-2-phenyl)ethyl]-3-{[(1S,2R)-2-(4,5-diphenyloxazol-2-yl)-1-cyclopentyl]methyl}benzamide IR (KBr, cm⁻¹): 3344, 3059, 3030, 2925, 2870, 1641, 1531, 1446, 1298

¹H-NMR (CDCl₃, δ): 1.33–1.55 (1H, m), 1.65–2.30 (5H, m), 2.55–3.03 (4H, m), 3.20–3.42 (1H, m), 3.57–3.78 (2H, m), 4.72–4.88 (1H, m), 6.52–6.70 (1H, m), 7.15–7.58 (19H, m)

MS (m/z): 543 (M+H)⁺

EXAMPLE 1-48

The following compound was obtained in a similar manner to that of Example 1-45.

N-[(1S)-(1-hydroxymethyl-2-phenyl)ethyl]-3-{[(1S,2R)-2-(4,5-diphenyloxazol-2-yl)-1-cyclopentyl]methyl}benzamide IR (KBr, cm⁻¹): 3330, 3059, 3028, 2925, 2868, 1639, 1533, 1446, 1294

¹H-NMR (CDCl₃, δ): 1.33–1.55 (1H, m), 1.65–2.30 (5H, m), 2.50–3.15 (6H, m), 3.42–3.70 (2H, m), 4.10–4.30 (1H, m), 6.36 (1H, d, J=7.4 Hz), 7.12–7.60 (19H, m)

MS (m/z): 557 (M+H)⁺

EXAMPLE 1-49

The following compound was obtained in a similar manner to that of Example 1-45.

4-{3-{[(1S,2R)-2-(4,5-diphenyloxazol-2-yl)-1-cyclopentyl]methyl}benzoyl}morpholine IR (KBr, cm⁻¹): 3055, 2956, 2920, 2854, 1635, 1442, 1417, 1277, 1113

¹H-NMR (CDCl₃, δ) 1.33–1.55 (1H, m), 1.65–2.32 (5H, m), 2.53–2.78 (2H, m), 2.83–3.07 (2H, m), 3.10–3.90 (8H, m), 7.10–7.45 (10H, m), 7.45–7.68 (4H, m)

MS (m/z): 493 (M+H)⁺

EXAMPLE 1-50

The following compound was obtained in a similar manner to that of Example 1-45.

N-(2,2-diphenylethyl)-3-{[(1S,2R)-2-(4,5-diphenyloxazol-2-yl)-1-cyclopentyl]methyl}benzamide IR (KBr, cm⁻¹): 3307, 3057, 3028, 2951, 2870, 1641, 1533, 1446, 1294

¹H-NMR (CDCl₃, δ): 1.33–1.53 (1H, m), 1.68–2.30 (5H, m), 2.48–3.02 (4H, m), 3.75–4.05 (2H, m), 4.21 (1H, t, J=7.8 Hz), 5.87–6.02 (1H, m), 7.13–7.63 (24H, m)

MS (m/z): 603 (M+H)⁺

EXAMPLE 1-51

The following compound was obtained in a similar manner to that of Example 1-45.

N,N-di-n-propyl-3-{[(1S,2R)-2-(4,5-diphenyloxazol-2-yl)-1-cyclopentyl]methyl}benzamide IR (neat, cm⁻¹): 3057, 2962, 2873, 1631, 1566, 1446, 1379, 1302, 1217

¹H-NMR (CDCl₃, δ): 0.58–1.10 (6H, m), 1.25–1.98 (8H, m), 1.98–2.30 (2H, m), 2.50–2.75 (2H, m), 2.90–3.20 (4H, m), 3.25–3.55 (2H, m), 7.10–7.42 (10H, m), 7.50–7.70 (4H, m)

MS (m/z): 507 (M+H)⁺

EXAMPLE 1-52

To a mixture of 3-{[(1S,2R)-2-(4,5-diphenyloxazol-2-yl)-1-cyclopentyl]methyl}benzoic acid (140 mg, 0.331 mmol), o-benzylhydroxylamine hydrochloride (69 mg, 0.430 mmol) and diisopropylethylamine (0.075 ml, 0.430 mmol) in DMF (5 ml) was added 1-hydroxybenzotrioxazole (67 mg, 0.497 mmol) and 1-ethyl-3-(3'-dimethylaminopropyl) carbodiimide hydrochloride (127 mg, 0.662 mmol). After stirring the mixture at room temperature for 2 hours, the reaction mixture was diluted with EtOAc (30 ml), washed with 1N hydrochloric acid, water, saturated sodium hydrogencarbonate solution, water, and brine. The resultant mixture was dried over magnesium sulfate, and evaporated in vacuo. The resultant residue was purified by silica gel column chromatography (hexane:EtOAc, 2:1 elution) to give N-benzyloxy-3-{[(1S,2R)-2-(4,5-diphenyloxazol-2-yl)-1-cyclopentyl]methyl}benzamide (170.5 mg, 98%).

IR (KBr, cm⁻¹): 3194, 3059, 3030, 2951, 2870, 1651, 1583, 1502, 1479, 1446, 1294

¹H-NMR (CDCl₃, δ): 1.36–1.55 (1H, m), 1.70–2.30 (5H, m), 2.57–3.02 (4H, m), 4.87 (1H, d, J=11.3 Hz), 4.93 (1H, d, J=11.3 Hz), 7.14–7.60 (19H, m), 8.56 (1H, s) MS (m/z): 529 (M+H)⁺

EXAMPLE 1-53

To a mixture of 3-{[(1S,2R)-2-(4,5-diphenyloxazol-2-yl)-1-cyclopentyl)methyl}benzoic acid (120 mg, 0.284 mmol) and 2-aminodiphenyl ether (68 ml, 0.369 mmol) in DMF (5 ml) was added 1-hydroxybenzotrioxazole (58 mg, 0.426 mmol), 1-ethyl-3-(3'-dimethylaminopropyl)carbodiimide hydrochloride (109 mg, 0.568 mmol), and 4-dimethylaminopyridine (27 mg, 0.284 mmol). After stirring the mixture at room temperature for 2 hours, the reaction mixture was heated at 80° C. for 3 hours. Then, the resultant mixture was diluted with EtOAc (30 ml), washed with 1N hydrochloric acid, water, saturated sodium hydrogencarbonate solution, water, and brine. The resultant mixture was dried over magnesium sulfate, and evaporated in vacuo. The residue was purified by silica gel column chromatography (hexane:EtOAc, 4:1 elution) to give N-(2-phenoxyphenyl)-3-{[(1S,2R)-2-(4,5-diphenyloxazol-2-yl)-1-cyclopentyl]methyl}benzamide (84.7 mg, 51%).

IR (neat, cm⁻¹): 3060, 2954, 2870, 1680, 1603, 1587, 1523, 1487, 1446

¹H-NMR (CDCl₃, δ): 1.35–1.55 (1H, m), 1.70–2.30 (5H, m), 2.54–3.05 (4H, m), 6.80–7.62 (22H, m), 8.36 (1H, s), 8.55 (1H, dd, J=8.0, 1.6 Hz)

MS (m/z): 591 (M+H)⁺

EXAMPLE 1-54

To a mixture of 3-{[(1S,2R)-2-(4,5-diphenyloxazol-2-yl)-1-cyclopentyl]methyl}benzoic acid (120 mg, 0.284 mmol) and 2-(2-methylaminoethyl)pyridine (0.047 ml, 0.341 mmol) in DMF (5 ml) was added 1-hydroxybenzotrioxazole (58 mg, 0.426 mmol) and 1-ethyl-3-(3'-dimethylaminopropyl)carbodiimide hydrochloride (109 mg, 0.568 mmol). After stirring the mixture at room temperature for 2 hours, the reaction mixture was diluted with EtOAc (30 ml), washed with water, saturated sodium hydrogencarbonate solution, water, and brine. The resultant mixture was dried over magnesium sulfate, and evaporated in vacuo. The resultant residue was purified by silica gel column chromatography (methylene chloride: MeOH, 15:1 elution), then treated with 4N hydrogen chloride in EtOAc (1ml) to give N-methyl-N-[2-(pyridin-2-yl)ethyl]-3-{[(1S,2R)-2-(4,5-diphenyloxazol-2-yl)-1-cyclopentyl]methyl}benzamide (140.9 mg, 86%).

IR (KBr, cm⁻¹): 3408, 3053, 2945, 2870, 2603, 1630, 1498, 1469, 1444, 1402

¹H-NMR (DMSO-d₆, δ): 1.30–1.52 (1H, m), 1.62–2.27 (5H, m), 2.40–3.10 (6H, m), 3.20–3.40 (3H, m), 3.70–3.92 (2H, m), 6.80–7.58 (14H, m), 7.75–8.08 (2H, m), 8.30–8.55 (1H, m), 8.65–8.85 (1H, m)

MS (m/z): 542 [(M+H)⁺-HCl]

EXAMPLE 1-55

The following compound was obtained in a similar manner to that of Example 1-54.

N-benzenesulfonyl-3-{[(1S,2R)-2-(4,5-diphenyloxazol-2-yl)-1-cyclopentyl]methyl}benzamide IR (Nujol, cm⁻¹): 1690

¹H-NMR (CDCl₃, δ): 1.6–2.3 (8H, m), 2.5–2.7 (11, m), 3.1–3.2 (1H, m), 6.94 (1H, m), 7.3–8.2 (19H, m)

MS (m/z): 563 (M+H)⁺

EXAMPLE 1-72

To a mixture of 3-{[(1S,2R)-2-(4,5-diphenyloxazol-2-yl)-1-cyclopentyl]methyl}benzoic acid (76 mg, 0.18 mmol) and (S)-2-amino-1-phenylethanol (30 mg, 0.22 mmol) in DMF (4 ml) was added 1-hydroxybenzotriazole (36 mg, 0.27 mmol) and 1-ethyl-3-(3'-dimethylaminopropyl) carbodiimide hydrochloride (69 mg, 0.36 mmol). After stirring the resulting mixture at room temperature for 2 hours, the reaction mixture was diluted with EtOAc (30 ml), washed with 1N-hydrochloric acid, water, saturated sodium hydrogencarbonate solution, water and brine successively, dried dried over magnesium sulfate, and evaporated in vacuo. The residue was purified by silica gel column chromatography (hexane:EtOAc, 1:1 elution) to give N-1(2S)-2-hydroxy-2-phenylethyl]-3-{[(1S,2R)-2-(4,5-diphenyloxazol-2-yl)-1-cyclopentyl]methyl}benzamide (92.8 mg, 95%).

IR (KBr, cm$^{-1}$): 3334, 3059, 3030, 2933, 2870, 1643, 1537, 1448, 1313

$^1$H-NMR (CDCl$_3$, δ): 1.32–1.60 (1H, m), 1.65–2.28 (5H, m), 2.55–3.03 (4H, m), 3.20–3.36 (1H, m), 3.63–3.78 (2H, m), 4.77–4.88 (1H, m), 6.60–6.73 (1H, m), 7.18–7.60 (19H, m)

MS (m/z): 543 (M+H$^+$)

EXAMPLES 2-1 TO 2-89

The following compound (Ib) was obtained according to the following Examples 2-1 to 2-89.

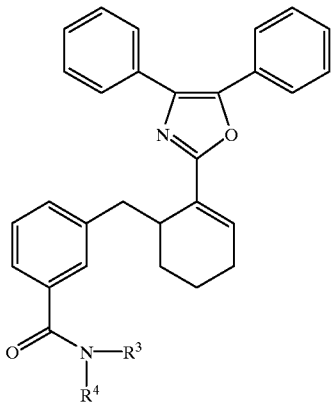
(Ib)

wherein R$^3$ and R$^4$ are as defined as the following Table 2.

Concerning each Example, the formula

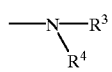

in the compound (Ib) and its MS spectrum were shown in Table 2.

TABLE 2

| Example No. | —N(R$^3$)(R$^4$) | MS(m/z) |
|---|---|---|
| 2-1 | N-methyl-N-cyclohexyl | 531 (M + H)$^+$ |
| 2-2 | N-H-N-(3-pyrrolidin-1-yl-propyl) | 546 (M + H)$^+$ |
| 2-3 | N-H-N-cyclohexyl | 517 (M + H)$^+$ |
| 2-4 | N-methyl-N-(2-hydroxyethyl) | 493 (M + H)$^+$ |
| 2-5 | N-methyl-N-(2-pyridin-2-yl-ethyl) | 554 (M + H)$^+$ |

TABLE 2-continued
| Example No. | —N(R³)(R⁴) | MS(m/z) |
|---|---|---|
| 2-6 | 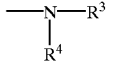 | 608 (M + H)⁺ |
| 2-7 | 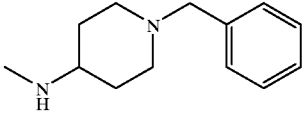 | 576 (M + H)⁺ |
| 2-8 | 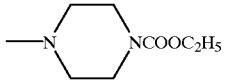 | 580 (M + H)⁺ |
| 2-9 | 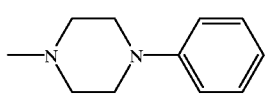 | 601 (M + H)⁺ |
| 2-10 | 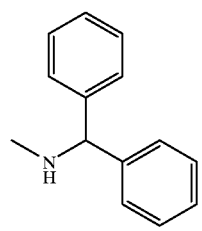 | 525 (M + H)⁺ |
| 2-11 | 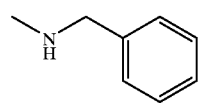 | 491 (M + H)⁺ |
| 2-12 | 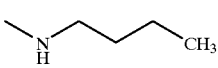 | 475 (M + H)⁺ |
| 2-13 | 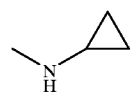 | 479 (M + H)⁺ |
| 2-14 | 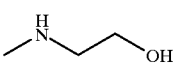 | 493 (M + H)⁺ |
| 2-15 | 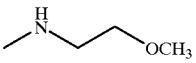 | 523 (M + H)⁺ |
| 2-16 | 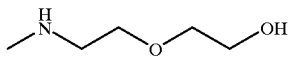 | 518 (M + H)⁺ |
| 2-17 | 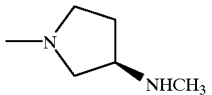 | 518 (M + H)⁺ |

TABLE 2-continued
| Example No. | —N(R³)(R⁴) | MS(m/z) |
|---|---|---|
| 2-18 | 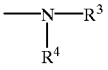 | 511 (M + H)⁺ |
| 2-19 | 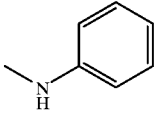 | 519 (M + H)⁺ |
| 2-20 | 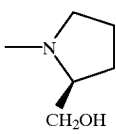 | 546 (M + H)⁺ |
| 2-21 | 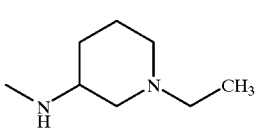 | 537 (M + H)⁺ |
| 2-22 | 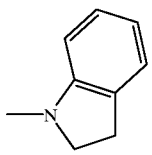 | 518 (M + H)⁺ |
| 2-23 |  | 546 (M + H)⁺ |
| 2-24 | 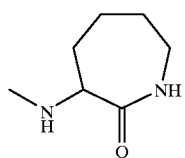 | 519 (M + H)⁺ |
| 2-25 | 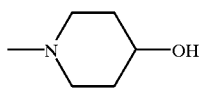 | 503 (M + H)⁺ |
| 2-26 | 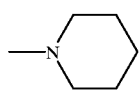 | 551 (M + H)⁺ |
| 2-27 | 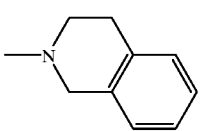 | 593 (M + H)⁺ |

TABLE 2-continued
| Example No. | —N(R³)(R⁴) | MS(m/z) |
|---|---|---|
| 2-28 | 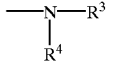 | 517 (M + H)⁺ |
| 2-29 | 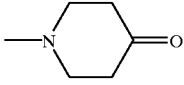 | 581 (M + H)⁺ |
| 2-30 | 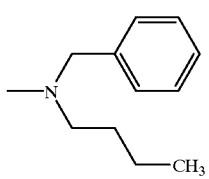 | 505 (M + H)⁺ |
| 2-31 | 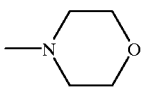 | 512 (M + H)⁺ |
| 2-32 | 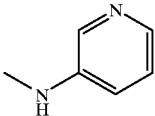 | 506 (M + H)⁺ |
| 2-33 | 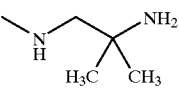 | 603 (M + H)⁺ |
| 2-34 | 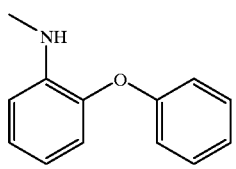 | 603 (M + H)⁺ |
| 2-35 | 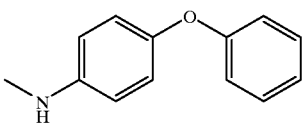 | 551 (M + H)⁺ |
| 2-36 | 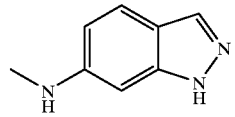 | 519 (M + H)⁺ |
| 2-37 | 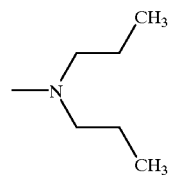 | 568 (M + H)⁺ |

TABLE 2-continued
| Example No. | —N(R³)(R⁴) | MS(m/z) |
|---|---|---|
| 2-38 | 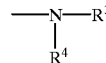 | 520 (M + H)+ |
| 2-39 | 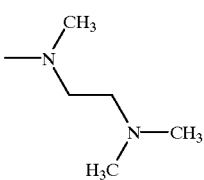 | 554 (M + H)+ |
| 2-40 | 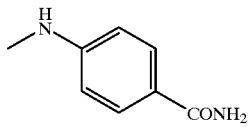 | 533 (M + H)+ |
| 2-41 | 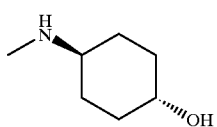 | 451 (M + H)+ |
| 2-42 |  | 465 (M + H)+ |
| 2-43 | 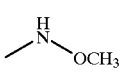 | 463 (M + H)+ |
| 2-44 | 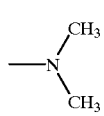 | 492 (M + H)+ |
| 2-45 | 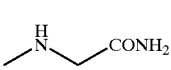 | 465 (M + H)+ |
| 2-46 | 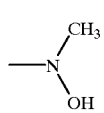 | 541 (M + H)+ |
| 2-47 | 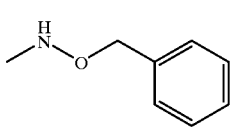 | 575 (M + H)+ |
| 2-48 | 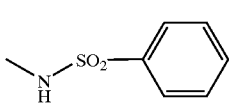 | 633 (M + Na)+ |
| 2-49 | 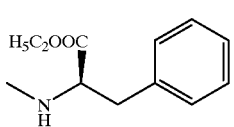 | 605 (M + Na)+ |

TABLE 2-continued
| Example No. | —N—R³ / R⁴ | MS(m/z) |
|---|---|---|
| 2-50 | 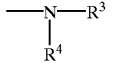 | 581 (M + Na)⁺ |
| 2-51 | 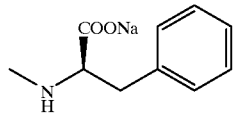 | 631 (M + Na)⁺ |
| 2-52 | 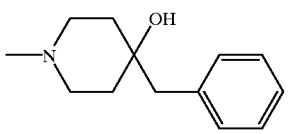 | 577 (M + Na)⁺ |
| 2-53 | 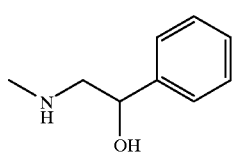 | 561 (M + Na)⁺ |
| 2-54 | 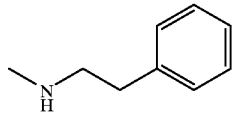 | 515 (M + Na)⁺ |
| 2-55 | 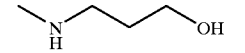 | 528 (M + Na)⁺ |
| 2-56 | 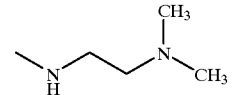 | 575 (M + Na)⁺ |
| 2-57 | 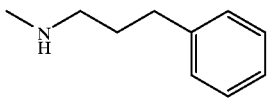 | 589 (M + Na)⁺ |
| 2-58 | 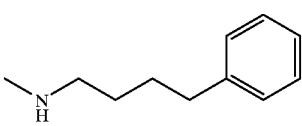 | 575 (M + Na)⁺ |
| 2-59 | 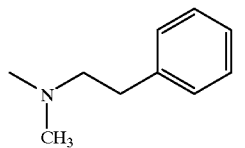 | 637 (M + Na)⁺ |

TABLE 2-continued
| Example No. | —N(R³)(R⁴) | MS(m/z) |
|---|---|---|
| 2-60 | 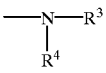 | 637 (M + Na)⁺ |
| 2-61 | 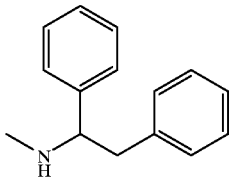 | 591 (M + Na)⁺ |
| 2-62 | 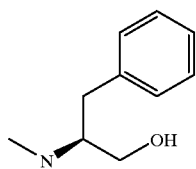 | 591 (M + Na)⁺ |
| 2-63 | 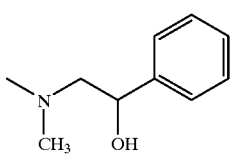 | 562 (M + Na)⁺ |
| 2-64 | 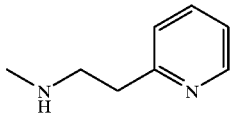 | 562 (M + Na)⁺ |
| 2-65 | 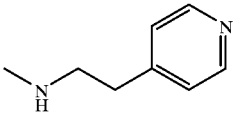 | 562 (M + Na)⁺ |
| 2-66 | 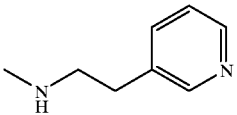 | 515 (M + Na)⁺ |
| 2-67 | 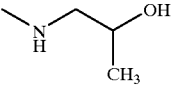 | 515 (M + Na)⁺ |
| 2-68 | 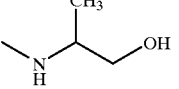 | 527 (M + Na)⁺ |
| 2-69 | 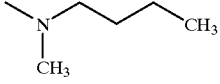 | 567 (M + Na)⁺ |

TABLE 2-continued
| Example No. | —N(R³)(R⁴) | MS(m/z) |
|---|---|---|
| 2-70 | 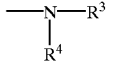 | 600 (M + Na)⁺ |
| 2-71 | 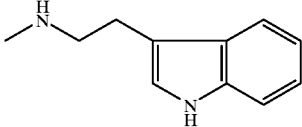 | 569 (M + Na)⁺ |
| 2-72 | 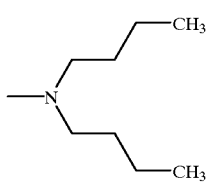 | 527 (M + Na)⁺ |
| 2-73 | 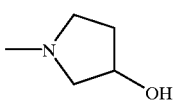 | 565 (M + Na)⁺ |
| 2-74 | 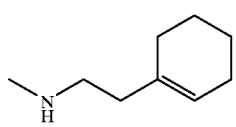 | 592 (M + H)⁺ |
| 2-75 | 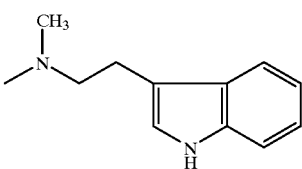 | 589 (M + H)⁺ |
| 2-76 | 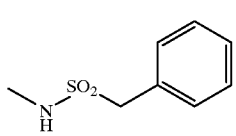 | 521 (M + H)⁺ |
| 2-77 | 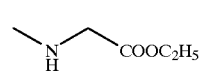 | 493 (M + H)⁺ |
| 2-78 | 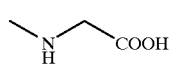 | 597 (M + H)⁺ |
| 2-79 | 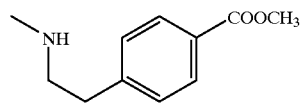 | 583 (M + H)⁺ |
| 2-80 | 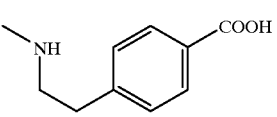 | 562 (M + H)⁺ |

TABLE 2-continued

| Example No. | —N(R³)(R⁴) | MS(m/z) |
|---|---|---|
| 2-81 | 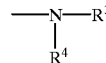 | 540 (M—HCl + H⁺) |
| 2-82 | 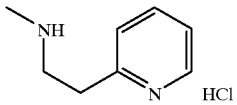 | 555 (M + H)⁺ |
| 2-83 | 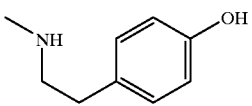 | 641 (M + H)⁺ |
| 2-84 | 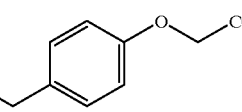 | 635 (M + H)⁺ |
| 2-85 | 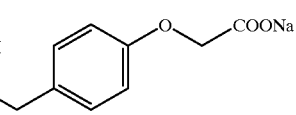 | 625 (M + H)⁺ |
| 2-86 | 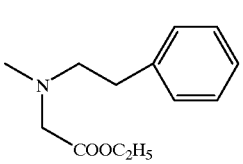 | 597 (M + H)⁺ |
| 2-87 | 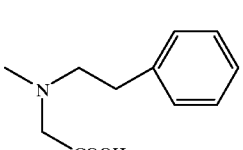 | 474 (M + H)⁺ |
| 2-88 | 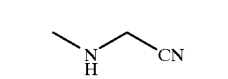 | 591 (M + H)⁺ |
| 2-89 | 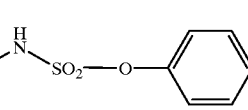 | 511 (M + H)⁻ |

EXAMPLES 2-1 TO 2-45 AND 2-51 TO 2-74

Coupling of (±)-3-{[2-(4,5-diphenyloxazol-2-yl)-2-cyclohexen-1-yl]methyl}benzoic acid with n different type of amines (n=69)

To a solution of (±)-3-{[2-(4,5-diphenyloxazol-2-yl)-2-cyclohexen-1-yl]methyl}benzoic acid (n×0.01 mmol) and 2-(1H-benzotrioxazol-1-yl)-1,1,3,3-tetramethyluronium tetrafluoroborate (TBTU) (n×0.015 mmol) in DMF (n×20 μl) was added a 1M DMF solution of diisopropylethylamine (n×14 μl), and the mixture was stirred at 27–30° C. for 1 hour. This activated acid solution was then distributed equally into n reaction vessels. To each reaction vessel was added 1M DMF or NMP solution of an amine [14 μl, n different type of amines (n=69)] and stirred at 27–30° C. for 2 hours.

To each reaction mixture was added 5% sodium hydrogencarbonate solution (0.40 ml), following by extraction with EtOAc (0.35 ml). The resultant aqueous layer was further extracted with EtOAc (0.20 ml×2). The combined organic layer was washed with water (0.30 ml). Then the resultant aqueous layer was additionally extracted with EtOAc (0.20 ml×2). The combined organic layer was concentrated by nitrogen flow and the resultant residue was dissolved in DMSO (1.0 ml) to give a ca. $10^{-2}$M DMSO solution of the above compound (Ib) which was subjected to analysis by MS spectrum.

EXAMPLE 2-46

To a mixture of 3-{[(1S)-2-(4,5-diphenyloxazol-2-yl)-2-cyclohexen-1-yl]methyl}benzoic acid (150 mg, 0.345 mmol), o-benzylhydroxylamine hydrochloride (61 mg, 0.379 mmol) and diisopropylethylamine (0.066 ml, 0.379 mmol) in DMF (5 ml) was added 1-hydroxybenzotrioxazole (52 mg, 0.379 mmol) and 1-ethyl-3-(3'-dimethylaminopropyl)carbodiimide hydrochloride (99 mg, 0.518 mmol). After stirring the mixture at room temperature for 1.5 hours, the reaction mixture was diluted with EtOAc (30 ml), washed with water, saturated sodium hydrogencarbonate solution, water, and brine. The resultant mixture was dried over magnesium sulfate, and evaporated in vacuo. The resultant residue was purified by silica gel column chromatography (hexane:EtOAc, 2:1 elution) to give N-benzyloxy-3-{[(1S)-2-(4,5-diphenyloxazol-2-yl)-2-cyclohexen-1-yl]methyl]benzamide (136.8 mg, 74%).

IR (KBr, cm$^{-1}$): 3251, 3030, 2931, 2858, 1647, 1504, 1444, 1298

$^1$H-NMR (CDCl$_3$, δ): 1.40–1.90 (4H, m), 2.20–2.40 (2H, m), 2.61 (1H, dd, J=13.0, 9.8 Hz), 3.07–3.25 (1H, m), 3.28 (1H, dd, J=13.0, 3.8 Hz), 4.98 (2H, s), 6.91 (1H, dd, J=3.8, 3.8 Hz), 7.22–7.75 (19H, m), 8.55 (1H, s)

MS (m/z): 541 (M+H)$^+$

EXAMPLE 2-47

The following compound was obtained in a similar manner to that of Example 2-46.

N-benzenesulfonyl-3-{[(1S)-2-(4,5-diphenyloxazol-2-yl)-2-cyclohexen-1-yl]methyl}benzamide IR (Nujol, cm$^{-1}$): 1670

$^1$H-NMR (CDCl$_3$, δ): 1.4–1.8 (4H, m), 2.2–2.4 (2H, m), 2.59 (1H, dd, J=13.0, 9.8 Hz), 3.0–3.3 (2H, m), 6.92 (1H, m), 7.2–8.2 (19H, m)

MS (m/z): 575 (M+H)$^+$

EXAMPLE 2-48

To a mixture of 3-{[2-(4,5-diphenyloxazol-2-yl)-2-cyclohexen-1-yl]methyl}benzoic acid (150 mg, 0.345 mmol), L-phenylalanine ethyl ester hydrochloride (103 mg, 0.448 mmol) and diisopropylethylamine (0.078 ml, 0.448 mmol) in DMF (5 ml) was added 1-hydroxybenzotrioxazole (70 mg, 0.518 mmol) and 1-ethyl-3-(3'-dimethylaminopropyl)carbodiimide hydrochloride (132 mg, 0.690 mmol). After stirring the mixture at room temperature for 4 hours, the reaction mixture was diluted with EtOAc (30 ml), washed with 1N hydrochloric acid, water, saturated sodium hydrogencarbonate solution, water, and brine. The resultant mixture was dried over magnesium sulfate, and evaporated in vacuo. The resultant residue was purified by silica gel column chromatography (hexane:EtOAc, 3:1 elution) to give ethyl (2S)-2-{3-{[2-(4,5-diphenyloxazol-2-yl)-2-cyclohexen-1-yl)methyl}benzoylamino}-3-phenylpropionate (197.1 mg, 94%).

IR (KBr, cm$^{-1}$): 3309, 2933, 1739, 1645, 1603, 1585, 1531, 1446

$^1$H-NMR (CDCl$_3$, δ): 1.20–1.34 (3H, m), 1.40–1.90 (4H, m), 2.05–2.50 (2H, m), 2.50–2.70 (1H, m), 3.10–3.43 (4H, m), 4.12–4.28 (2H, m), 4.98–5.10 (1H, m), 6.54–6.65 (1H, m), 6.89–6.97 (1H, m), 7.08–7.77 (19H, m)

MS (m/z): 633 (M+Na)$^+$

EXAMPLE 2-49

To a solution of ethyl (2S)-2-{3-{[2-(4,5-diphenyloxazol-2-yl)-2-cyclohexen-1-yl]methyl}benzoylamino}-3-phenylpropionate (119 mg, 0.195 mmol) in tetrahydrofuran (4 ml) was added a solution of lithium hydroxide-water (16.4 mg, 0.390 mmol) in MeOH-water (1:1) (2.8 ml) at 5° C. The reaction mixture was stirred at the same temperature for 1 hour, and then stirred at room temperature for 30 minutes. To the reaction mixture was added 1N hydrochloric acid (0.5 ml) at 5° C. and extracted with EtOAc. The organic layer was washed with water and brine. The resultant mixture was dried over magnesium sulfate, and evaporated in vacuo to give (2S)-2-{3-{[2-(4,5-diphenyloxazol-2-yl)-2-cyclohexen-1-yl]methyl}-benzoylamino}-3-phenylpropionic acid (113.0 mg, 100%).

IR (KBr, cm$^{-1}$) 3413, 2933, 1732, 1641, 1525, 1446

$^1$H-NMR (CDCl$_3$, δ): 1.40–1.95 (4H, m), 2.05–2.50 (2H, m), 2.50–2.73 (1H, m), 3.05–3.40 (4H, m), 4.87–5.03 (1H, m), 6.60–6.85 (1H, m), 6.85–6.98 (1H, m), 7.08–7.75 (19H, m)

MS (m/z): 605 (M+Na)$^+$

EXAMPLE 2-50

To a solution of (2S)-2-{3-{[2-(4,5-diphenyloxazol-2-yl)-2-cyclohexen-1-yl)methyl}benzoylamino}-3-phenylpropionic acid (85.4 mg, 0.147 mmol) in MeOH (3 ml) was added 1N sodium hydroxide (0.147 ml, 0.147 mmol) at 5° C. The reaction mixture was stirred at the same temperature for 30 minutes, and evaporated in vacuo. To the residue was added ethyl ether, and the resulting solid was collected by filtration to give sodium (2S)-2-{3-{[2-(4,5-diphenyloxazol-2-yl)-2-cyclohexen-1-yl]methyl}benzoylamino}-3-phenylpropionate (84.9 mg, 96%).

IR (KBr, cm$^{-1}$): 3357, 2931, 2860, 1643, 1601, 1531, 1446, 1400

$^1$H-NMR (DMSO-d$_6$, δ): 1.30–1.93 (4H, m), 2.05–2.70 (3H, m), 2.93–3.35 (4H, m), 4.05–4.21 (1H, m), 6.87–6.97 (1H, m), 7.08–7.78 (20H, m)

MS (m/z): 581 (M–Na)$^{31}$

EXAMPLE 2-75

To a mixture of 3-{[(1S)-2-(4,5-diphenyloxazol-2-yl)-2-cyclohexen-1-yl]methyl}benzoic acid (250 mg, 0.575 mmol) and α-toluenesulfonamide (98 mg, 0.575 mmol) in DMF (6 ml) was added 4-dimethylaminopyridine (105 mg, 0.863 mmol) and 1-ethyl-3-(3'-dimethylaminopropyl) carbodiimide hydrochloride (220 mg, 1.15 mmol). After stirring the resulting mixture at room temperature for 16 hours, the reaction mixture was diluted with EtOAc (30 ml), washed with 1N-hydrochloric acid, water and brine successively, dried over dried over magnesium sulfate, and evaporated in vacuo. The residue was purified by silica gel column chromatography (hexane:EtOAc, 1:1 elution) to give N-benzylsulfonyl-3-{[(1S)-2-(4,5-diphenyloxazol-2-yl)-2-cyclohexen-1-yl]methyl}benzamide (216.4 mg, 64%).

IR (KBr, cm$^{-1}$): 3244, 3060, 2933, 1693, 1450, 1344, 1155

$^1$H-NMR (CDCl$_3$, δ): 1.45–1.90 (4H, m), 2.08–2.50 (2H, m), 2.62 (1H, dd, J=13.0, 10.1 Hz), 3.05–3.22 (1H, m), 3.27 (1H, dd, J=13.0, 3.6 Hz), 4.67 (1H, d, J=14.0 Hz), 4.77 (1H, d, J=14.0 Hz), 6.93 (1H, dd, J=3.9, 3.9 Hz), 7.20–7.80 (19H, m), 8.85 (1H, br)

MS (m/z): 589 (M+H$^+$)

EXAMPLE 2-76

To a mixture of (±)-3-{[2-(4,5-diphenyloxazol-2-yl)-2-cyclohexen-1-yl]methyl}benzoic acid (150 mg, 0.345 mmol), glycine ethyl ester hydrochloride (63 mg, 0.449 mmol) and diisopropylethylamine (0.078 ml, 0.449 mmol)

in DMF (5 ml) was added 1-hydroxybenzotriazole (70 mg, 0.518 mmol) and 1-ethyl-3-(3'-dimethylaminopropyl) carbodiimide hydrochloride (132 mg, 0.690 mmol). After stirring the resulting mixture at room temperature for 3 hours, the reaction mixture was diluted with EtOAc (30 ml), washed with 1N-hydrochloric acid, water, saturated sodium hydrogencarbonate solution, water and brine successively, dried over magnesium sulfate, and evaporated in vacuo. The residue was purified by silica gel column chromatography (hexane:EtOAc, 2:1 elution) to give ethyl (±)-{3-{[2-(4,5-diphenyloxazol-2-yl)-2-cyclohexen-1-yl]methyl}-benzoylamino}acetate (168.9 mg, 94%).

IR (KBr, cm$^{-1}$): 3332, 3055, 2933, 1749, 1649, 1533, 1196

$^1$H-NMR (CDCl$_3$, δ): 1.31 (3H, t, J=7.1 Hz), 1.40–1.90 (4H, m), 2.08–2.45 (2H, m), 2.64 (1H, dd, J=13.0, 9.8 Hz), 3.10–3.38 (2H, m), 4.02–4.13 (2H, m), 4.25 (2H, q, J=7.1 Hz), 6.53–6.70 (1H, m), 6.88–6.96 (1H, m), 7.18–7.80 (14H, m)

MS (m/z): 521 (M+H$^+$)

EXAMPLE 2-77

To a solution of ethyl (±)-{3-{[2-(4,5-diphenyloxazol-2-yl)-2-cyclohexen-1-yl]methyl}benzoylamino}acetate (136.8 mg, 0.263 mmol) in tetrahydrofuran (4 ml) was added a solution of lithium hydroxide-water (22.1 mg, 0.526 mmol) in MeOH-water (1:1) (2.8 ml) at 5° C. and the mixture was stirred at room temperature for 2 hours. To the reaction mixture was added 1N-hydrochloric acid (0.8 ml) at 5° C. and extracted with EtOAc. The organic layer was washed with water and brine successively, dried over magnesium sulfate, and evaporated in vacuo to give (±)-{3-{[2-(4,5-diphenyloxazol-2-yl)-2-cyclohexen-1-yl]methyl}benzoylamino}acetic acid (129.0 mg, 100%).

IR (KBr, cm$^{-1}$): 3346, 3055, 2933, 1732, 1645, 1535

$^1$H-NMR (CDCl$_3$, δ): 1.50–1.95 (4H, m), 2.10–2.50 (2H, m), 2.68 (1H, dd, J=14.9, 10.4 Hz), 3.10–3.30 (2H, m), 3.85–4.30 (2H, m), 6.82–7.00 (2H, m), 7.18–7.75 (14H, m)

MS (m/z): 493 (M+H$^+$)

Preparation 10

To a solution of tyramine (3.0 g, 21.9 mmol) in tetrahydrofuran (30 ml) was added di-tert-butyl dicarbonate (5.26 g, 24.1 mmol) at 5° C. and the mixture was stirred at room temperature for 1 hour. The solvent was removed in vacuo and the residue was diluted with EtOAc, washed with water and brine, dried over magnesium sulfate, and evaporated in vacuo. The residue was purified by silica gel column chromatography (hexane:EtOAc, 3:1–2:1 elution) to give tert-butyl [2-(4-hydroxyphenyl)ethyl]carbamate (5.77 g, 111%) as an oil.

IR (neat, cm$^{-1}$): 3346, 2978, 2933, 1685, 1614, 1514, 1450, 1367

$^1$H-NMR (CDCl$_3$, δ): 1.44 (9H, s), 2.71 (2H, t, J=7.0 Hz), 3.24–3.40 (2H, m), 4.48–4.62 (1H, m), 5.43 (1H, s), 6.77 (2H, d, J=8.5 Hz), 7.04 (2H, d, J=8.5 Hz)

MS (m/z): 138 (M–C$_5$H$_9$O$_2$+2H)$^+$

Preparation 11

To a solution of tert-butyl[2-(4-hydroxyphenyl)-ethyl]carbamate (5.69 g, 24.0 mmol) and 2,6-lutidine (5.59 ml, 48.0 mmol) in methylene chloride (85 ml) was added trifluoromethanesulfonic anhydride (5.0 ml, 29.7 mmol) at 5° C. and the mixture was stirred for 30 min. The solvent was removed in vacuo and the residue was diluted with EtOAc, washed with 1N-hydrochloric acid, water, saturated sodium hydrogencarbonate solution, water and brine successively, dried over magnesium sulfate, and evaporated in vacuo. The residue was purified by silica gel column chromatography (hexane:EtOAc, 5:1) to give 4-[2-(tert-butoxycarbonylamino)-ethyl]phenyl trifluoromethane-sulfonate (6.15 g, 69%).

IR (KBr, cm$^{-1}$): 3383, 2987, 1682, 1527, 1417, 1250

$^1$H-NMR (CDCl$_3$, δ): 1.43 (9H, s), 2.83 (2H, t, J=7.0 Hz), 3.28–3.45 (2H, m), 4.43–4.63 (1H m), 7.14–7.34 (4H,m)

MS (m/z): 270 (M–C$_5$H$_9$O$_2$+2H)$^+$

Preparation 12

A mixture of 4-[2-(tert-butoxycarbonylamino)ethyl]-phenyl trifluoromethanesulfonate (6.11 g, 16.6 mmol), palladium(II) acetate (745 mg, 3.32 mmol), 1,3-bis-(diphenylphosphino)propane (1.37 g, 3.32 mmol), triethylamine (6.94 ml, 49.8 mmol), and MeOH (24ml) in DMF (60 ml) was purged for 30 min with carbon monoxide. The mixture was stirred under carbon monoxide atmosphere at 78° C. for 3 hours. After cooling the mixture to room temperature, the reaction mixture was diluted with EtOAc, washed with water, 1N-hydrochloric acid, water, saturated sodium hydrogencarbonate, water and brine successively, dried over magnesium sulfate, and evaporated in vacuo. The residue was purified by silica gel column chromatography (hexane:EtOAc, 4:1–3:1) to give methyl 4-[2-(tert-butoxycarbonylamino)ethyl]benzoate (3.52 g, 76%).

IR (KBr, cm$^{-1}$): 3371 , 2978, 2947, 1722, 1680, 1525, 1277

$^1$H-NMR (CDCl$_3$, δ): 1.43 (9H, s), 2.86 (2H, t, J=7.0 Hz),3.32–3.45 (2H, m), 3.91 (3H, s), 4.45–4.63 (1H, m), 7.27 (2H, d, J=8.3 Hz), 7.98 (2H, d, J=8.3 Hz)

MS (m/z): 1 80 (M–C$_5$H$_9$O$_2$+2H)$^+$

Preparation 13

To a solution of methyl 4-[2-(tert-butoxycarbonylamino) ethyl]benzoate (3.50 g, 12.5 mmol) in methylene chloride (35 ml) was added 4N hydrogen chloride in 1,4-dioxane (35 ml) at 5° C. and the mixture was stirred for 30 min. The solvent was removed in vacuo and the resulting solid was collected, washed with isopropyl ether and dried to give methyl 4-(2-aminoethyl)-benzoate hydrochloride (2.63 g, 97%).

IR (KBr, cm$^{-1}$): 2970, 1726, 1606, 1466, 1435, 1281

$^1$H-NMR (DMSO-d$_6$, δ): 2.92–3.20 (4H, m), 3.85 (3H, s), 7.43 (2H, d, J=8.3 Hz), 7.93 (2H, d, J=8.3 Hz), 8.14 (3H, br)

MS (m/z): 180 (M–HCl+H$^+$)

EXAMPLE 2-78

The following compound was obtained in a similar manner to that of Example 2-76.

methyl (±)-4-{2-{3-{[2-(4,5-diphenyloxazol-2-yl)-2-cyclohexen-1-yl]methyl}benzoylamino}ethyl}benzoate IR (KBr, cm$^{-1}$): 3329, 2927, 2856, 1716, 1635, 1535, 1444, 1275

$^1$H-NMR (DMSO-d$_6$, δ): 1.35–1.90 (4H, m), 2.03–2.50 (2H, m), 2.50–2.70 (1H, m), 2.93 (2H, t, J=6.9 Hz), 2.99–3.35 (2H, m), 3.40–3.62 (2H, m), 3.82 (3H,s), 6.88–6.97 (1H, m), 7.30–7.72 (15H, m), 7.75 (1H, s), 7.89 (2H, d, J=8.2 Hz), 8.53 (1H, t, J=5.6 Hz)

MS (m/z): 597 (M+H$^+$)

EXAMPLE 2-79

The following compound was obtained in a similar manner to that of Example 2-77.

(±)-4-{2-{3-{[2-(4,5-diphenyloxazol-2-yl)-2-cyclohexen-1-yl]-methyl}benzoylamino}ethyl}benzoic acid IR (KBr, cm$^{-1}$): 3319, 2933, 1691, 1635, 1537, 1284

¹H-NMR (DMSO-d₆, δ): 1.35–1.98 (4H, m), 2.05–2.50 (2H, m), 2.50–2.70 (1H, m), 2.80–3.00 (2H, m), 3.00–3.60 (4H, m), 6.88–6.95 (1H, m), 7.28–7.72 (15H,m), 7.76 (1H, s), 7.87 (2H, d, J=8.2 Hz), 8.45–8.60 (1H, m)

MS (m/z) 583 (M+H⁺)

EXAMPLE 2-80

To a mixture of (S)-3-{[2-(4,5-diphenyloxazol-2-yl)-2-cyclohexen-1-yl]methyl}benzoic acid (120 mg, 0.276 mmol) and 2-(2-aminoethyl)pyridine (0.040 ml, 0.331 mmol) in DMF (5 ml) was added 1-hydroxybenzotriazole (56 mg, 0.414 mmol) and 1-ethyl-3-(3'-dimethylaminopropyl)carbodiimide hydrochloride (106 mg, 0.552 mmol). After stirring the resulting mixture at room temperature for 2 hours, the reaction mixture was diluted with EtOAc (30 ml), washed with water, saturated sodium hydrogencarbonate solution, water and brine successively, dried over magnesium sulfate, and evaporated in vacuo. The residue was purified by silica gel column chromatography (methylene chloride:MeOH, 20:1 elution) to give (S)-N-[2-(2-pyridyl)ethyl]-3-{[2-(4,5-diphenyloxazol-2-yl)-2-cyclohexen-1-yl]methyl}benzamide (138.8 mg, 93%).

¹H-NMR (CDCl₃, δ): 1.40–1.90 (4H, m), 2.10–2.50 (2H, m), 2.62 (1H, dd, J=13.3, 11.5 Hz), 3.07 (2H, t, J=6.3 Hz), 3.13–3.43 (2H, m), 3.76–3.90 (2H, m), 6.89–6.97 (1H, m), 7.05–7.78 (18H, m), 8.47–8.56 (1H, m)

EXAMPLE 2-81

To a solution of (S)-N-[2-(2-pyridyl)ethyl]-3-{[2-(4,5-diphenyloxazol-2-yl)-2-cyclohexen-1-yl]methyl}benzamide (130 mg, 0.241 mmol) in ethyl ether (4 ml) was added 4N hydrogen chloride in EtOAc (0.5 ml) at room temperature. The solvent was removed in vacuo and the resulting solid was collected, washed with ethyl ether, and dried to give (S)-N-[2-(2-pyridyl)ethyl]-3-{[2-(4,5-diphenyloxazol-2-yl)-2-cyclohexen-1-yl]methyl}benzamide hydrochloride (135.2 mg, 97%).

IR (KBr, cm⁻¹) 3292, 3055, 2933, 1645, 1535, 1298, 1066

¹H-NMR (DMSO-d₆, δ) 1.35–1.95 (4H, m), 2.05–2.50 (2H, m), 2.55–2.70 (1H, m), 2.98–3.40 (4H, m), 3.60–3.83 (2H, m), 6.88–6.95 (1H, m), 7.25–7.78 (14H, m), 7.80–8.00 (2H, m), 8.39–8.53 (1H, m), 8.58–8.73 (1H, m), 8.73–8.88 (1H, m)

MS (m/z): 540(M–HCl+H⁺)

EXAMPLE 2-82

To a mixture of (±)-3-{[2-(4,5-diphenyloxazol-2-yl)-2-cyclohexen-1-yl]methyl}benzoic acid (300 mg, 0.690 mmol) and tyramine (123 mg, 0.897 mmol) in DMF (5 ml) was added 1-hydroxybenzotriazole (140 mg, 1.04 mmol) and 1-ethyl-3-(3'-dimethylaminopropyl)carbodiimide hydrochloride (265 mg, 1.38mmol). After stirring the resulting mixture at room temperature for 3 hours, the reaction mixture was diluted with EtOAc (30 ml), washed with 1N-hydrochloric acid, water, saturated sodium hydrogencarbonate solution, water and brine successively, dried over magnesium sulfate, and evaporated in vacuo. The residue was purified by silica gel column chromatography (hexane:EtOAc, 3:2 elution) to give (±)-N-[2-(4-hydroxyphenyl)ethyl]-3-{[2-(4,5-diphenyloxazol-2-yl)-2-cyclohexen-1-yl]methyl}benzamide (358.4 mg, 94%).

IR (KBr, cm⁻¹): 3336, 2933, 1633, 1537, 1514, 1444, 1309, 1232

¹H-NMR (DMSO-d₆, δ): 1.38–2.08 (4H, m), 2.08–2.50 (2H, m), 2.50–2.80 (3H, m), 3.00–3.50 (4H, m), 6.68 (2H, d, J=8.4 Hz), 6.88–6.98 (1H, m), 7.03 (2H, d, J=8.4 Hz), 7.25–7.74 (13H, m), 7.79 (1H, s), 8.49 (1H, t, J=5.4 Hz), 9.17 (1H, s)

MS (m/z): 555 (M+H⁺)

EXAMPLE 2-83

To a mixture of (±)-N-[2-(4-hydroxyphenyl)ethyl]-3-[2-(4,5-diphenyloxazol-2-yl)-2-cyclohexen-1-yl]methyl}benzamide (120 mg, 0.217 mmol) and potassium carbonate (60 mg, 0.434 mmol) in DMF (4 ml) was added ethyl bromoacetate (0.048 ml, 0.435 mmol) and stirred at room temperature for 17 hours. The reaction mixture was diluted with EtOAc, washed with water and brine successively, dried over magnesium sulfate, and evaporated in vacuo. The residue was purified by silica gel column chromatography (hexane:EtOAc, 3:1–2:1) to give ethyl (±)-4-{2-{3-{[2-(4,5-diphenyloxazol-2-yl)-2-cyclohexen-1-yl]methyl}benzoylamino}ethyl}phenoxyacetate (130.0 mg, 94%).

IR (KBr, cm⁻¹): 3309, 2931, 1757, 1643, 1535, 1510

¹H-NMR (CDCl₃, δ) 1.29 (3H, t, J=7.1 Hz), 1.40–1.95 (4H, m), 2.05–2.45 (2H, m), 2.62 (1H, dd, J=13.0, 9.9 Hz), 2.80 (2H, t, J=7.0 Hz), 3.06–3.25 (1H, m), 3.30 (1H, dd, J=13.0, 3.5 Hz), 3.47–3.67 (2H, m), 4.26 (2H, q, J=7.1 Hz), 4.58 (2H, s), 6.11 (1H, t, J=6.1 Hz), 6.85 (2H, d, J=8.7 Hz), 6.87–6.97 (1H, m), 7.13 (2H, d, J=8.7 Hz), 7.20–7.74 (14H, m)

MS (m/z): 641 (M+H⁺)

EXAMPLE 2-84

To a solution of ethyl (±)-4-{2-{3-{[2-(4,5-diphenyloxazol-2-yl)-2-cyclohexen-1-yl]methyl}-benzoylamino}ethyl}phenoxyacetate (115 mg, 0.18 mmol) in MeOH-1,4-dioxane (1:1, 4 ml) was added 1N sodium hydroxide solution (0.18 ml, 0.18 mmol) at 5° C. and the mixture was stirred at room temperature for 2 hours. The reaction mixture was evaporated and Et₂O was added thereto. The resulting solid was collected by filtration to give sodium (±)-4-{2-{3-{[2-(4,5-diphenyloxazol-2-yl)-2-cyclohexen-1-yl]methyl}-benzoylamino}ethyl}phenoxyacetate (105.0 mg, 92%).

IR (KBr, cm⁻¹): 3334, 2929, 1639, 1604, 1512, 1425

¹H-NMR (DMSO-d₆, δ): 1.35–1.95 (4H, m), 2.10–2.83 (5H, m), 3.00–3.50 (4H, m), 4.03 (2H, s) 6.73 (2H, d, J=8.5 Hz), 6.85–6.95 (1H, m), 7.08 (2H, d, J=8.5 Hz), 7.30–7.73 (13H, m) 7.80 (1H, s), 8.48–8.62 (1H, m)

MS (m/z): 635 (M+H⁺)

Preparation 14

To a solution of 2-phenylethylamine (3.0 g, 24.8 mmol) in DMF (30 ml) was added ethyl bromoacetate (3.0 ml, 27.3 mmol) at 5° C. Then triethylamine (4.15 ml, 29.8 mmol) was added thereto at the same temperature. After stirring the resulting mixture at room temperature for 18 hours, the reaction mixture was diluted with EtOAc, washed with water and brine successively, dried over magnesium sulfate, and evaporated in vacuo. The residue was purified by silica gel column chromatography (methylene chloride:MeOH, 20:1) to give ethyl phenethylaminoacetate (1.87 g, 37%) as an oil.

IR (neat, cm⁻¹): 3028, 2935, 1738, 1454, 1201, 1146, 1028

¹H-NMR (CDCl₃, δ): 1.26 (3H, t, J=7.1 Hz), 2.74–2.94 (4H, m), 3.41 (2H,s), 4.17 (2H, q, J=7.1 Hz), 7.15–7.35 (5H, m)

MS (m/z): 208 (M+H⁺)

EXAMPLE 2-85

The following compound was obtained in a similar manner to that of Example 2-82.

Ethyl (±)-{3-{(2-(4,5-diphenyloxazol-2-yl)-2-cyclohexen-1-yl]methyl}benzoyl}-N-phenethylaminoacetate IR (KBr, cm$^{-1}$): 2933, 1745, 1643, 1446, 1200

$^1$H-NMR (CDCl$_3$, δ): 1.13–1.38 (3H, m), 1.38–1.90 (4H, m), 2.05–2.45 (2H, m), 2.45–2.63 (1H, m), 2.63–3.08 (2H, m), 3.08–3.43 (2H, m), 3.43–4.35 (6H, m), 6.85–7.00 (2H, m), 7.10–7.55 (14H, m), 7.55–7.78 (4H, m)

MS (m/z): 625 (M+H$^+$)

EXAMPLE 2-86

The following compound was obtained in a similar manner to that of Example 2-77.

(±)-{3-{[2-(4,5-diphenyloxazol-2-yl)-2-cyclohexen-1-yl]methyl}benzoyl}-N-phenethylaminoacetic acid IR (KBr, cm$^{-1}$): 3028, 2931, 1738, 1643, 1599, 1448, 1196

$^1$H-NMR (CDCl$_3$, δ) 1.38–1.95 (4H, m), 1.95–2.45 (2H, m), 2.45–4.30 (9H, m), 6.80–7.00 (2H, m), 7.05–7.77 (18H, m)

MS (m/z) 597 (M+H$^+$)

EXAMPLE 2-87

The following compound was obtained in a similar manner to that of Example 2-76.

(±)-N-cyanomethyl-3-{[2-(4,5-diphenyloxazol-2-yl)-2-cyclohexen-1-yl]methyl}benzamide IR (KBr, cm$^{-1}$): 3320, 3053, 2933, 2251, 1651, 1529, 1296

$^1$H-NMR (CDCl$_3$, δ): 1.50–1.90 (4H, m), 2.10–2.50 (2H, m), 2.58–2.78 (1H, m), 3.10–3.30 (2H, m), 3.98 (1H, dd, J=17.4, 5.7 Hz), 4.18 (1H, dd, J=17.4, 6.0 Hz), 6.55–6.67 (1H, m), 6.92 (1H, dd, J=4.0, 4.0 Hz), 7.25–7.73 (14H, m)

MS (m/z): 474 (M+H$^+$)

Preparation 15

To a solution of phenol (5.01 g, 53.2 mmol) in toluene (25 ml) was added a solution of chlorosulfonyl isocyanate (7.9 g, 55.9 mmol) in toluene (30 ml) at room temperature. The mixture was stirred at 120° C. for 14 hours. The solvent was removed in vacuo and the residue was added dropwise to water (75 ml). After stirring the resultant mixture at room temperature for 24 hours, the resulting precipitate was collected, washed with water, dissolved in EtOAc, washed with brine successively, dried over magnesium sulfate, and evaporated in vacuo. The residue was purified by silica gel column chromatography (hexane:EtOAc, 1:1) to give sulfamic acid phenyl ester (5.52 g, 60%).

IR (KBr, cm$^{-1}$): 3421, 3309, 1595, 1550, 1489, 1367

$^1$H-NMR (CDCl$_3$, δ) 4.99 (2H, brs), 7.26–7.50 (5H, m)

MS (m/z): 172 (M–H)$^-$

EXAMPLE 2-88

The following compound was obtained in a the similar manner to that of Example 2-76.

Phenyl (±)-{3-{[2-(4,5-diphenyloxazol-2-yl)-2-cyclohexen-1-yl]methyl}benzoyl}sulfamate IR (KBr, cm$^{-1}$): 3454, 3059, 2933, 1707, 1593, 1554, 1487, 1444, 1348

$^1$H-NMR (CDCl$_3$, δ) 1.25–1.78 (4H, m), 2.00–2.33 (2H, m), 2.33–2.55 (1H, m), 2.98–3.1 8 (2H, m), 6.75–6.85 (1H, m), 6.90–7.65 (17H, m), 7.75 (1H, d, J=7.8 Hz), 7.87 (1H, s)

MS (m/z): 591 (M+H$^+$)

EXAMPLE 2-89

The following compound was obtained in a similar manner to that of Example 2-76.

(±)-N-methylsulfony-3-{[2-(4,5-diphenyloxazol-2-yl)-2-cyclohexen-1-yl]methyl}benzamide IR (KBr, cm$^{-1}$): 3243, 3032, 2933, 1695, 1604, 1533, 1446, 1402, 1342

$^1$H-NMR (CDCl$_3$, δ): 1.42–2.05 (4H, m), 2.10–2.53 (2H, m), 2.67 (1H, dd, J=11.7, 8.0 Hz), 3.08–3.40 (2H, m), 3.25 (3H, s), 6.94 (1H, dd, J=3.8, 3.8 Hz), 7.24–7.74 (13H, m), 7.79 (1H, s), 9.22 (1H, br)

MS (m/z): 511 (M–H)$^-$

Preparation 16

To a solution of 1-(3,5-dimethoxybenzyl)-2-(4,5-diphenyloxazol-2-yl)-2-cyclohexene (8.3 g) in methylene chloride (100 ml) was added boron tribromide (55 ml, 1M solution in methylene chloride) at 0° C. After stirring the mixture for 2 hours, the solvent was evaporated in vacuo. The residue was diluted with EtOAc, and the reaction mixture was washed with water and brine. The dried solvent was evaporated in vacuo, and then dissolved in metylene chloride (50 ml). To the solution were added trifluoromethanesulfonic acid anhydride (9.3 ml) and 2,6-lutidine (8.6 ml) at –78° C. After stirring the mixture for 2 hours, the solvent was evaporated in vacuo. The residue was diluted with EtOAc, and the reaction mixture was washed with water, saturated sodium hydrogencarbonate and brine. The dried solvent was evaporated in vacuo. The residue was purified by chromatography on silica gel to give 1-(3,5-ditrifluoromethanesulfonyloxybenzyl)-2-(4,5-diphenyloxazol-2-yl)-2-cyclohexene (9 g).

To a solution of 1-(3,5-ditrifluoromethanesulfonyloxybenzyl)-2-(4,5-diphenyloxazol-2-yl)-2-cyclohexene (9 g) in a mixture of ethanol (30 ml) and DMF (40 ml) was added 1,3-bis(diphenylphosphino)propane (1.8 g), palladium acetate (0.96 g), and triethylamine (15 ml). After stirring the mixture for 5 hours at 80° C. under CO atmosphere, the resultant mixture was partitioned between EtOAc and water, and then the organic layer was washed with 1N-hydrochloric acid, saturated sodium hydrogencarbonate, and brine. The dried solvent was evaporated in vacuo. The obtained solid was washed with ether to afford diethyl 5-{[2-(4,5-diphenyloxazol-2-yl)-2-cyclohexen-1-yl]methyl}isophthalate (4.1 g)

IR (Nujol, cm$^{-1}$): 1720

$^1$H-NMR (CDCl$_3$, δ): 1.38 (6H, t, J=8 Hz), 1.4–2.0 (4H, m), 2.2–2.4 (2H, m), 2.71 (1H, dd, J=10,12 Hz), 3.1–3.3 (1H, m), 3.36 (1H, dd, J=4,12 Hz), 4.38 (4H, q, J=8 Hz), 6.92 (1H, m), 7.2–7.8 (10H, m), 8.22 (2H, J=2 Hz), 8.47 (1H, m)

MS (m/z): 536 (M+H)$^+$

EXAMPLE 3

Diethyl 5-{[2-(4,5-diphenyloxazol-2-yl)-2-cyclohexen-1-yl]-methyl}isophthalate acid was hydrolyzed in a similar manner to that of Preparation 8, and then the resulting compound was subjected to amide reaction of protected carboxy group in a similar manner to that of Example 1-46 to give 3-[N-(2-phenylethyl)carbamoyl]-5-{[2-(4,5-diphenyloxazol-2-yl)-2-cyclohexen-1-yl]methyl}benzoic acid.

IR (Nujol, cm$^{-1}$) 1698, 1648

$^1$H-NMR (CDCl$_3$, δ): 1.4–2.0 (4H, m), 2.2–2.4 (2H, m), 2.5–3.0 (3H, m), 3.0–3.7 (4H, m), 6.25 (1H, m), 6.93 (1H, m), 7.1–7.5 (10H, m), 7.5–7.8 (2H, m), 8.0–8.2 (1H, m)

MS (m/z) 583 (M+H)+

EXAMPLE 4

The following compound was obtained in a similar manner to that of Example 2-82.

N-phenethyl-3-{[2-(4,5-diphenyloxazol-2-yl)-1-cyclohexen-1-yl]methyl}benzamide

IR (KBr, cm$^{-1}$): 3307, 3059, 3026, 2929, 2858, 1639, 1537, 1444, 1298

$^1$H-NMR (CDCl$_3$, δ): 1.45–1.85 (4H, m), 2.05–2.20 (2H, m), 2.58–2.75 (2H, m), 2.84 (2H, t, J=7.0 Hz), 3.55–3.70 (2H, m), 4.05 (2H, s), 5.98–6.15 (1H, m), 7.13–7.77 (19H, m)

MS (m/z): 539 (M+H$^+$)

EXAMPLE 5

The following compound was obtained in a similar manner to that of Example 2-82.

N-phenethyl-3{[2-(4,5-diphenyloxazol-2-yl)-1-cyclopenten-1-yl]methyl}benzamide

IR (KBr, cm$^{-1}$): 3286, 3057, 2949, 1635, 1541, 1323

$^1$H-NMR (CDCl$_3$, δ): 1.84–2.03 (2H, m), 2.40–2.57 (2H, m), 2.86 (2H, t, J=7.0 Hz), 2.90–3.05 (2H, m), 3.58–3.74 (2H, m), 4.17 (2H, s), 6.02–6.14 (1H, m), 7.15–7.77 (19H, m)

MS (m/z): 525 (M+H$^+$)

Preparation 17

A mixture of 3-{(2-(4,5-diphenyloxazol-2-yl)-2-cyclohexen-1-yl]methyl}benzoic acid (2.60 g, 5.98 mmol), triethylamine (1.08 ml, 7.77 mmol), and diphenylphosphoryl azide (1.67 ml, 7.77 mmol) in t-butanol-toluene (2:1, 80 ml) was stirred at 80° C. for 18 hours. After cooling the mixture to room temperature, the mixture was evaporated, diluted with EtOAc, washed with saturated sodium hydrogencarbonate solution, water and brine, dried over magnesium sulfate, and evaporated in vacuo. The residue was purified by silica gel column chromatography (hexane:EtOAc, 8:1 elution) to give {3-{[2-(4,5-diphenyloxazol-2-yl)-2-cyclohexen-1-yl]methyl}phenyl}carbamic acid tert-butyl ester (2.36 g, 78%).

IR (KBr, cm$^{-1}$): 3327, 2976, 2931, 1728, 1608, 1593, 1531, 1489, 1442

$^1$H-NMR (CDCl$_3$, δ): 1.40–1.86 (4H, m), 1.52 (9H, s), 2.05–2.35 (2H, m), 2.52 (1H, dd, J=12.8, 10.0 Hz), 3.06–3.30 (2H, m), 6.40 (1H, s), 6.86–6.95 (1H, m), 6.95–7.05 (1H, m), 7.15–7.45 (9H, m), 7.57–7.75 (4H, m)

MS (m/z): 507 (M+H$^+$)

Preparation 18

To a solution of {3-{[2-(4,5-diphenyloxazol-2-yl)-2-cyclohexen-1-yl]methyl}phenyl}carbamic acid tert-butyl ester (2.34 g, 4.62 mmol) in methylene chloride (25 ml) was added trifluoroacetic acid (7 ml) at 5° C. and the mixture was stirred at room temperature for 1.5 hour. After evaporation, the residue was dissolved in EtOAc, and saturated sodium hydrogencarbonate solution was added thereto under ice-cooling. The mixture was extracted with EtOAc, washed with water and brine, dried over magnesium sulfate, and evaporated in vacuo. The residue was purified by silica gel column chromatography (hexane:EtOAc, 3:1 elution) to give 3-{[2-(4,5-diphenyloxazol-2-yl)-2-cyclohexen-1-yl]methyl}phenylamine (1.74 g, 93%).

IR (KBr, cm$^{-1}$): 3454, 3357, 2931, 1603, 1531, 1495, 1444, 1242

$^1$H-NMR (DMSO-d$_6$, δ): 1.30–1.90 (4H, m), 2.03–2.67 (3H, m), 2.92–3.18 (2H, m), 4.97 (2H, s), 6.34–6.55 (3H, m), 6.82–7.02 (2H, m), 7.30–7.55 (6H, m), 7.55–7.70 (4H, m)

MS (m/z): 407 (M+H$^+$)

Preparation 19

To a solution of 2-phenylethylamine (0.082 ml, 0.65 mmol) and triethylamine (0.097 ml, 070 mmol) in methylene chloride (3 ml) was added a solution of crude 3-{[2-(4,5-diphenyloxazol-2-yl)-2-cyclohexen-1-yl]methyl}benzenesulfonyl chloride (213 mg, 0.44 mmol) in [ethylene]methylene chloride (3 ml) at 5° C. After stirring at room temperature for 1 hour, the reaction mixture was diluted with EtOAc, washed with 1N hydrochloric acid, water, saturated sodium hydrogencarbonate solution, water and brine, dried over magnesium sulfate, and evaporated in vacuo. The residue was purified by silica gel column chromatography (hexane:EtOAc, 5:1–3:1 elution) to give 3-{[2-(4,5-diphenyloxazol-2-yl)-2-cyclohexen-1-yl]methyl}-N-(phenethyl)benzenesulfonamido (54.3 mg, 22%).

EXAMPLE 6-1

To a solution of 2-phenylethylamine (0.082 ml, 0.65 mmol) and triethylamine (0.097 ml, 0.70 mmol) in methylene chloride (3 ml) was added a solution of crude 3-{[2-(4,5-diphenyloxazol-2-yl)-2-cyclohexen-1-yl]methyl}benzenesulfonyl chloride (213 mg, 0.44 mmol) in methylene chloride (3 ml) at 5° C. After stirring at room temperature for 1 hour, the reaction mixture was diluted with EtOAc, washed with 1N hydrochloric acid, water, saturated sodium hydrogencarbonate solution, water and brine, dried over magnesium sulfate, and evaporated in vacuo. The residue was purified by silica gel column chromatography (hexane:EtOAc, 5:1–3:1 elution) to give 3-{[2-(4,5-diphenyloxazol-2-yl)-2-cyclohexen-1-yl]methyl}-N-(phenethyl)benzenesulfonamide (54.3 mg, 22%).

IR (KBr, cm$^{-1}$): 3276, 3059, 3028, 2933, 2862, 1601, 1533, 1446, 1331, 1153

$^1$H-NMR (CDCl$_3$, δ): 1.20–1.90 (4H, m), 2.05–2.50 (2H, m), 2.62 (1H, dd, J=13.4, 10.5 Hz), 2.71 (2H, t, J=6.7 Hz), 3.05–3.27 (3H, m), 3.36 (1H, dd, J=13.4, 2.9 Hz), 4.28 (1H, t, J=6.3 Hz), 6.85–7.08 (3H, m), 7.10–7.85 (17H, m)

MS (m/z): 575 (M+H$^+$)

EXAMPLE 6-2

To a mixture of 28% ammonia solution (0.7 ml) and MeOH (1.0 ml) was added a solution of crude 3-{[2-(4,5-diphenyloxazol-2-yl)-2-cyclohexen-1-yl]methyl}-benzenesulfonyl chloride (253 mg, 0.52 mmol) in tetrahydrofuran (3 ml) at 5° C. After stirring at room temperature for 30 min, the reaction mixture was diluted with EtOAc, washed with 1N hydrochloric acid, water, saturated sodium hydrogencarbonate solution, water and brine, dried over magnesium sulfate, and evaporated in vacuo. The residue was purified by silica gel column chromatography (hexane:EtOAc, 2:1 elution) to give 3-{[2-(4,5-diphenyloxazol-2-yl)-2-cyclohexen-1-yl]methyl}benzenesulfonamide (41.3 mg, 17%).

IR (KBr, cm$^{-1}$): 3319, 3236, 2935, 1529, 1444, 1306, 1159

$^1$H-NMR (DMSO-d$_6$, δ): 1.30–2.00 (4H, m), 2.00–2.45 (2H, m), 2.55–2.75 (1H, m), 2.95–3.15 (1H, m), 3.18–3.40 (1H, m), 6.94 (1H, dd, J=3.7, 3.7 Hz), 7.20–7.77 (13H, m), 7.85 (1H, s)

MS (m/z): 471 (M+H$^+$)

EXAMPLE 7-1

To a mixture of (±)-3-{[2-(4,5-diphenyloxazol-2-yl)-2-cyclohexen-1-yl]methyl}phenylamine (130 mg, 0.32 mmol)

and 3-phenylpropionic acid (58 mg, 0.38 mmol) in DMF (4 ml) was added 1-hydroxybenzotriazole (65 mg, 0.48 mmol) and 1-ethyl-3-(3'-dimethylaminopropyl)carbodiimide hydrochloride (123 mg, 0.64 mmol). After stirring the mixture at room temperature for 1 hour, the reaction mixture was diluted with EtOAc, washed with 1N hydrochloric acid, water, saturated sodium hydrogencarbonate solution, water and brine, dried over magnesium sulfate, and evaporated in vacuo. The residue was purified by silica gel column chromatography (hexane-EtOAc, 3:1 elution) to give (±)-N-{{3-[2-(4,5-diphenyloxazol-2-yl)-2-cyclohexen-1-yl]methyl}phenyl}-3-phenylpropionamide (141.4 mg, 82%).

IR (KBr, cm$^{-1}$): 3290, 3026, 2931, 2860, 1660, 1608, 1550, 1533, 1485, 1442

$^1$H-NMR (CDCl$_3$, δ): 1.35–1.93 (4H, m), 2.05–2.40 (2H, m), 2.45–2.75 (3H, m), 2.90–3.30 (4H, m), 6.80–7.65 (17H, m), 7.65–7.77 (4H, m)

MS (m/z): 539 (M+H$^+$)

EXAMPLE 7-2

The following compound was obtained in a similar manner to that of Example 7-1.

(±)-N-{{3-[2-(4,5-diphenyloxazol-2-yl)-2-cyclohexen-1-yl]methyl}phenyl}-3-phenylacrylamide IR (KBr, cm$^{-1}$): 3276, 3055, 2931, 2860, 1662, 1626, 1608, 1550, 1487, 1444

$^1$H-NMR (CDCl$_3$, δ): 1.40–1.90 (4H, m), 2.10–2.45 (2H, m), 2.58 (1H, dd, J=12.5, 9.3 Hz), 3.10–3.33 (2H, m), 6.47 (1H, d, J=15.5 Hz), 6.92 (1H, dd, J=4.0, 4.0 Hz), 7.05–7.16 (1H, m), 7.18–7.78 (20H, m)

MS (m/z): 537 (M+H$^+$)

EXAMPLE 7-3

To a solution of (±)-3-{[2-(4,5-diphenyloxazol-2-yl)-2-cyclohexen-1-yl]methyl}phenylamine (110 mg, 0.27 mmol) in methylene chloride (3 ml) was added benzoylisocyanate (0.038 ml, 0.27 mmol) at 5° C., and the mixture was stirred at room temperature for 16 hours. To the mixture was added hexane (9 ml), and the resulting precipitate was collected, washed with hexane to give (±)-1-benzoyl-3-{3-{[2-(4,5-diphenyloxazol-2-yl)-2-cyclohexen-1-yl]methyl}phenyl}urea (114.9 mg, 77%).

IR (KBr, cm$^{-1}$): 3248, 2935, 1701, 1606, 1562, 1475, 1267, 1225

$^1$H-NMR (DMSO-d$_6$, δ) 1.35–1.95 (4H, m), 2.08–2.70 (3H, m), 2.95–3.40 (2H, m), 6.83–6.95 (1H, m), 7.00–7.13 (1H, m), 7.20–7.75 (16H, m), 7.95–8.12(2H, m), 10.85(1H, s), 11.00(1H, s)

MS (m/z): 554 (M+H$^+$)

EXAMPLE 7-4

To a solution of (±)-3-{[2-(4,5-diphenyloxazol-2-yl)-2-cyclohexen-1-yl]methyl}phenylamine (110 mg, 0.27 mmol) in methylene chloride (3 ml) was added benzylisocyanate (0.17 ml, 1.36 mmol) at 5° C., and the mixture was stirred at room temperature for 30 min. The reaction mixture was diluted with EtOAc, washed with 1N hydrochloric acid, water, saturated sodium hydrogencarbonate solution, water and brine, dried over magnesium sulfate, and evaporated in vacuo. The resulting solid was collected and washed with EtOAc-hexane to give (±)-1-benzyl-3-{3-{[2-(4,5-diphenyloxazol-2-yl)-2-cyclohexen-1-yl]methyl}phenyl}urea (100.7 mg, 69%).

IR (KBr, cm$^{-1}$): 3302, 3030, 2931, 1635, 1566, 1442, 1238

$^1$H-NMR (DMSO-d$_6$, δ): 1.30–1.95 (4H, m), 2.05–2.70 (3H, m), 2.94–3.23 (2H, m), 4.32(2H, d, J=6.0 Hz), 6.58(1H, t, J=6.0 Hz), 6.77–6.95 (2H, m), 7.08–7.53 (14H, m), 7.53–7.73 (4H, m), 8.56 (1H, s)

MS (m/z): 540 (M+H$^+$)

EXAMPLE 7-5

To a solution of (±)-3-{[2-(4,5-diphenyloxazol-2-yl)-2-cyclohexen-1-yl]methyl}phenylamine (110 mg, 0.27 mmol) in methylene chloride (3 ml) was added benzenesulfonylisocyanate (0.037 ml, 0.27 mmol) at 5° C., and the mixture was stirred at room temperature for 1 hour. The reaction mixture was evaporated, and the residue was purified by silica gel column chromatography (methylene chloride-MeOH, 30:1 elution) to give (±)-1-benzenesulfonyl-3-{3-{[2-(4,5-diphenyloxazol-2-yl)-2-cyclohexen-1-yl]methyl}phenyl}urea (159.0 mg, 100%).

IR (KBr, cm$^{-1}$): 3338, 2933, 1689, 1612, 1595, 1552 1487, 1446, 1346, 1242

$^1$H-NMR (CDCl$_3$, δ): 1.35–1.95 (4H, m), 2.05–2.43 (2H, m), 2.43–2.63 (1H, m), 3.09–3.34(2H, m), 6.86–6.96 (1H, m), 7.05–7.75 (18H, m), 7.83–7.99 (2H, m), 8.37 (1H, br s)

MS (m/z): 590 (M+H$^+$)

EXAMPLE 7-6

To a mixture of (±)-3-{[2-(4,5-diphenyloxazol-2-yl)-2-cyclohexen-1-yl]methyl}phenylamine (110 mg, 0.27 mmol) and pyridine (0.066ml, 0.81 mmol) in methylene chloride (3 ml) was added benzylsulfonyl chloride (78 mg, 0.41 mmol) at 5° C. The mixture was stirred at the same temperature for 30 min, then stirred at room temperature for 30 min. The reaction mixture was diluted with EtOAc, washed with 1N hydrochloric acid, water, saturated sodium hydrogencarbonate solution, water and brine, dried over magnesium sulfate, and evaporated in vacuo. The residue was purified by silica gel column chromatography (hexane-EtOAc, 5:1 elution) to give (±)-N-3-{[2-(4,5-diphenyloxazol-2-yl)-2-cyclohexen-1-yl]methyl}phenyl}benzylsulfonamide (99.2 mg, 65%).

IR (KBr, cm$^{-1}$): 3251, 3033, 2931, 1604, 1589, 1496, 1444, 1400, 1338, 1244, 1151

$^1$H-NMR (CDCl$_3$, δ): 1.42–1.92 (4H, m), 2.10–2.45 (2H, m), 2.56 (1H, dd, J=13.0, 10.3 Hz), 3.10–3.38 (2H, m), 4.30 (2H, m), 6.16 (1H, s), 6.90–7.45 (16H, m), 7.53–7.75 (4H, m)

MS (m/z): 561 (M+H$^+$)

What is claimed is:

1. A compound of the formula:

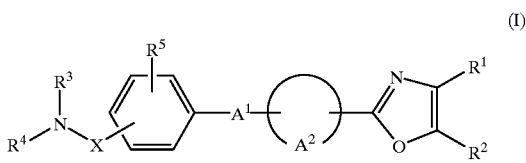

(I)

wherein

R$^1$ is aryl which is unsubstituted or substituted with halogen(s),

R$^2$ is aryl which is unsubstituted or substituted with halogen(s),

X is single bond

or SO$_2$,

R$^3$ and R$^4$ are independently hydrogen or suitable substituent, (wherein X is

neither R$^3$ nor R$^4$ is hydrogen),

R$^3$ and R$^4$, when linked together form

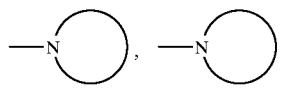

is N-containing heterocyclic group which is unsubstituted or substituted with one or more suitable substituent(s), R$^5$ is
(1) hydrogen,
(2) hydroxy,
(3) carboxy, or
(4) protected carboxy, A$^1$ is lower alkylene or single bond,

is cyclo(C$_3$–C$_9$)alkane or cyclo(C$_5$–C$_9$)alkene, or a pharmaceutically acceptable salt thereof.

2. A compound according to the claim 1, wherein

R$^1$ is aryl which is unsubstituted or substituted with halogen(s),

R$^2$ is aryl which is unsubstituted or substituted with halogen(s),

X is single bond,

or SO$_2$,

R$^3$ and R$^4$ are independently
(1) hydrogen;
(2) hydroxy;
(3) lower alkyl which is unsubstituted or substituted with one or more substituent(s) selected from the group consisting of:
 (a) hydroxy,
 (b) cyano,
 (c) lower alkoxy,
 (d) hydroxy(lower)alkoxy,
 (e) cyclo(lower)alkyl,
 (f) cyclo(lower)alkenyl,
 (g) amino,
 (h) lower alkylamino,
 (i) carbamoyl,
 (j) carboxy,
 (k) protected carboxy,
 (l) heterocyclic group optionally substituted with ar(lower)alkyl or oxo, and
 (m) aryl optionally substituted with
  hydroxy,
  carboxy,
  protected carboxy,
  carboxy(lower)alkyl, or
  lower alkoxy which is unsubstituted or substituted with carboxy or protected carboxy;
(4) lower alkoxy which is unsubstituted or substituted with aryl(s);
(5) aryl which is unsubstituted or substituted with one or more substituent(s) selected from the group consisting of:
 (a) aryloxy,
 (b) acylamino, and
 (c) carbamoyl;
(6) cyclo(lower)alkyl which is unsubstituted or substituted with hydroxy(s);
(7) arylsulfonyl;
(8) ar(lower)alkylsulfonyl;
(9) lower alkylsulfonyl;
(10) aryloxysulfonyl;
(11) heterocyclic group which is unsubstituted or substituted with one or more substituent(s) selected from the group consisting of:
 (a) ar(lower)alkyl,
 (b) aryl,
 (c) protected carboxy,
 (d) lower alkyl, and
 (e) oxo;
(12) acyl which is unsubstituted or substituted with aryl; or
(13) carbamoyl which is unsubstituted or substituted with acyl, ar(lower)alkyl, or arylsulfonyl, (wherein X is

neither R$^3$ nor R$^4$ is hydrogen),

R$^3$ and R$^4$, when linked together form

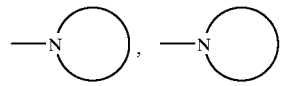

is N-containing heterocyclic group which is unsubstituted or substituted with one or more substituent(s) selected from the group consisting of:
(1) lower alkyl,
(2) aryl,
(3) protected carboxy,
(4) hydroxy(lower)alkyl,
(5) ar(lower)alkyl,
(6) hydroxy,
(7) oxo, and
(8) lower alkylamino, R$^5$ is (1) hydrogen,
(2) hydroxy,
(3) carboxy, or
(4) protected carboxy, $A^1$ is lower alkylene or single bond,

is cyclo($C_3$–$C_9$)alkane or cyclo($C_5$–$C_9$)alkene,
or a pharmaceutically acceptable salt thereof.

3. A compound according to the claim 1, wherein $R^1$ is aryl,
$R^2$ is aryl,
X is single bond,

or $SO_2$, $R^3$ and $R^4$ are independently
(1) hydrogen;
(2) hydroxy;
(3) lower alkyl which is unsubstituted or substituted with one or more substituent(s) selected from the group consisting of:
  (a) hydroxy,
  (b) cyano,
  (c) lower alkoxy,
  (d) hydroxy(lower)alkoxy,
  (e) cyclo(lower)alkyl,
  (f) cyclo(lower)alkenyl,
  (g) amino,
  (h) lower alkylamino,
  (i) carbamoyl,
  (j) carboxy,
  (k) protected carboxy,
  (l) heterocyclic group optionally substituted with ar(lower)alkyl or oxo, and
  (m) aryl optionally substituted with hydroxy, carboxy,
    protected carboxy,
    carboxy(lower)alkyl, or
    lower alkoxy which is unsubstituted or substituted with carboxy or protected carboxy;
(4) lower alkoxy which is unsubstituted or substituted with aryl(s);
(5) aryl which is unsubstituted or substituted with one or more substituent(s) selected from the group consisting of:
  (a) aryloxy,
  (b) acylamino, and
  (c) carbamoyl;
(6) cyclo(lower)alkyl which is unsubstituted or substituted with hydroxy(s);
(7) arylsulfonyl;
(8) ar(lower)alkylsulfonyl;
(9) lower alkylsulfonyl;
(10) aryloxysulfonyl;
(11) heterocyclic group which is unsubstituted or substituted with one or more substituent(s) selected from the group consisting of:
  (a) ar(lower)alkyl,
  (b) aryl,
  (c) protected carboxy,
  (d) lower alkyl, and
  (e) oxo;
(12) acyl which is unsubstituted or substituted with aryl; or
(13) carbamoyl which is unsubstituted or substituted with acyl, ar(lower)alkyl, or arylsulfonyl, (wherein X is

neither $R^3$ nor $R^4$ is hydrogen), $R^3$ and $R^4$, when linked together form

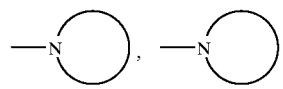

is N-containing heterocyclic group which is unsubstituted or substituted with one or more substituent(s) selected from the group consisting of:
(1) lower alkyl,
(2) aryl,
(3) protected carboxy,
(4) hydroxy(lower)alkyl,
(5) ar(lower)alkyl,
(6) hydroxy,
(7) oxo, and
(8) lower alkylamino, $R^5$ is hydrogen,
$A^1$ is lower alkylene,

is
(1) cyclohexane,
(2) cyclohexene,
(3) cyclopentane, or
(4) cyclopentene,
or a pharmaceutically acceptable salt thereof.

4. A compound according to the claim 1, wherein $R^1$ is phenyl,
$R^2$ is phenyl,
X is

or $SO_2$, $R^3$ and $R^4$ are independently
(1) hydrogen;
(2) lower alkyl which is unsubstituted or substituted with one or more substituent(s) selected from the group consisting of:
  (a) hydroxy, (b) heterocyclic group, and
(c) phenyl;
(3) lower alkoxy which is unsubstituted or substituted with phenyl; or
(4) phenyl which is unsubstituted or substituted with phenyloxy;
(wherein X is

neither $R^3$ nor $R^4$ is hydrogen),
$R^3$ and $R^4$ are linked together to form

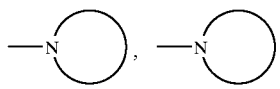

is N-containing heterocyclic group;
$R^5$ is hydrogen,
$A^1$ is methylene,

is
(1) is cyclohexane,
(2) cyclohexene,
(3) cyclopentane, or
(4) cyclopentene,
or a pharmaceutically acceptable salt thereof.

5. A compound according to the claim 1,
wherein said compound is N-((2-hydroxy-2-phenyl)ethyl]-3-{[(1S,2R)-2-(4,5-diphenyloxazol-2-yl)-1-cyclopentyl]methyl}benzamide, N-(2,2-diphenylethyl)-3-{[(1S,2R)-2-(4,5-diphenyl-oxazol-2-yl)-1-cyclopentyl]methyl}benzamide, N-benzyloxy-3-{[(1S)-2-(4,5-diphenyloxazol-2-yl)-2-cyclohexen-1-yl]methyl}benzamide or N-benzylsulfonyl-3-{[(1S)-2-(4,5-diphenyloxazol-2-yl)-2-cyclohexen-1-yl]methyl}benzamide.

6. A process for preparing the compound of the formula (1):

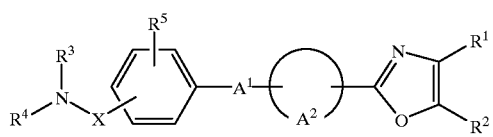

wherein
$R^1$ is aryl which is unsubstituted or substituted with halogen(s),
$R^2$ is aryl which is unsubstituted or substituted with halogen(s), X is single bond,

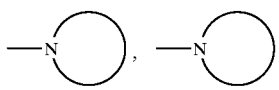

or $SO_2$,
$R^3$ and $R^4$ are independently hydrogen or suitable substituent,
(wherein X is

neither $R^3$ nor $R^4$ is hydrogen),
$R^3$ and $R^4$, when linked together form

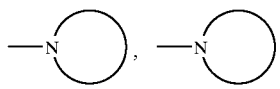

is N-containing heterocyclic group which is unsubstituted or substituted with one or more suitable substituent(s),
$R^5$ is
(1) hydrogen,
(2) hydroxy,
(3) carboxy, or
(4) protected carboxy,
$A^1$ is lower alkylene or single bond,

is cyclo($C_3$–$C_9$)alkane or cyclo($C_5$–$C_9$)alkene,
or a pharmaceutically acceptable salt thereof, which comprises,
(1) reacting a compound of the formula (II):

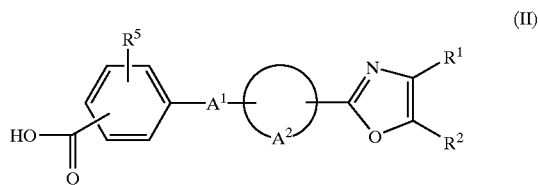

wherein $R^1$, $R^2$, $R^5$, $A^1$, and $A^2$ are each as defined above, or a salt thereof with a compound of the formula (III):

(III)

$$\begin{array}{c} R^3 \\ / \\ NH \\ \backslash \\ R^4 \end{array}$$

wherein $R^3$ and $R^4$ are each as defined above, or its reactive derivative at the amino group or a salt thereof to give a compound of the formula (IV):

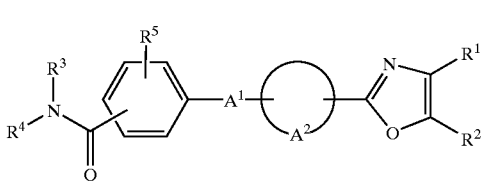

(IV)

wherein $R^1$, $R^2$, $R^3$, $R^4$, $R^5$, $A^2$, and $A^2$ are each as defined above, or a pharmaceutically acceptable salt thereof; or (2) reacting a compound of the formula (V):

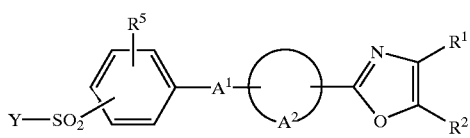

(V)

wherein $R^1$, $R^2$, $R^5$, $A^2$, and $A^2$ are each as defined above,

Y is halogen, or a salt thereof with a compound of the formula (III):

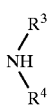

(III)

wherein $R^3$ and $R^4$ are each as defined above, or its reactive derivative at the amino group or a salt thereof to give a compound of the formula (VI):

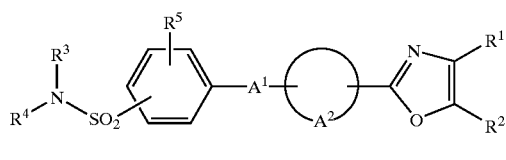

(VI)

wherein $R^1$, $R^2$, $R^3$, $R^4$, $R^5$, $A^1$, and $A^2$ are each as defined above, or a pharmaceutically acceptable salt thereof; or (3) reacting a compound of the formula (VII):

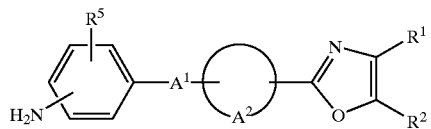

(VII)

wherein $R^1$, $R^2$, $R^5$, $A^1$, and $A^2$ are each as defined above, or a salt thereof with a compound of the formula (VIII):

(VIII)

wherein $R^{4a}$ is acyl which is unsubstituted or substituted with aryl, or its reactive derivative at the carboxy group or a salt thereof to give a compound of the formula (IX):

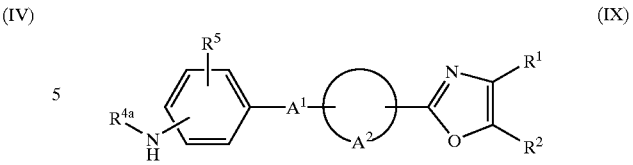

(IX)

wherein $R^1$, $R^2$, $R^{4a}$, $R^5$, $A^1$, and $A^2$ are each as defined above, or a pharmaceutically acceptable salt thereof; or (4) reacting a compound of the formula (VII):

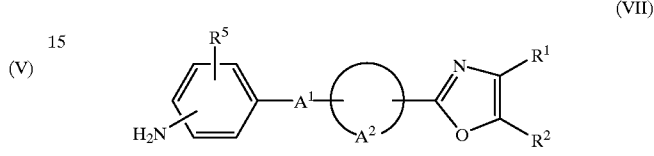

(VII)

wherein $R^1$, $R^2$, $R^5$, $A^1$, and $A^2$ are each as defined above, or a salt thereof with a compound of the formula (X):

$R^6$—NCO (X)

wherein $R^6$ is acyl or hydroxy, or a salt thereof to give a compound of the formula (XI):

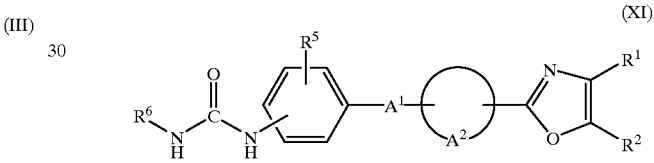

(XI)

wherein $R^1$, $R^2$, $R^5$, $R^6$, $A^1$, and $A^2$ are each as defined above, or a pharmaceutically acceptable salt thereof; or (5) reacting a compound of the formula (VII):

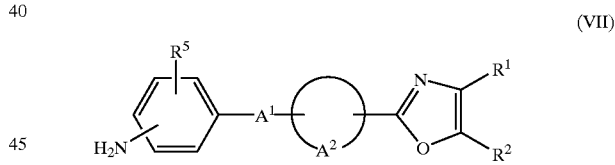

(VII)

wherein $R^1$, $R^2$, $R^5$, $A^1$, and $A^2$ are each as defined above, or a salt thereof with a compound of the formula (XII):

$R^7$—$SO_3H$ (XII)

wherein $R^7$ is lower alkyl, ar(lower)alkyl or aryl, or its reactive derivative at the sulfo group or a salt thereof to give a compound of the formula (XIII):

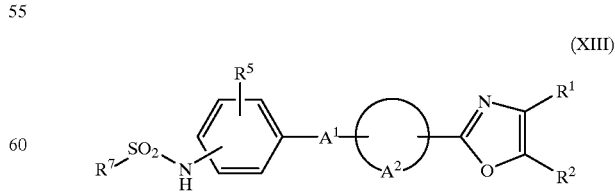

(XIII)

wherein $R^1$, $R^2$, $R^5$, $R^7$, $A^1$, and $A^2$ are each as defined above, or a pharmaceutically acceptable salt thereof.

7. A pharmaceutical composition which comprises, as an active ingredient, a compound of claim 1 or a pharmaceutically acceptable salt thereof in admixture with pharmaceutically accetpable carriers.

8. A method for treating $PGE_2$ mediated diseases which comprises administering an effective amount of the compound of claim 1 to human beings or animals.

9. A method for treating inflammatory conditions, various pains, collagen diseases, autoimmune diseases, various immunity diseases, analgesic, thrombosis, allergic disease, cancer or neurodegenerative diseases which comprises administering an effective amount of the compound of claim 1 to human beings or animals.

10. A method for treating mesangial proliferative glomerulonephritis, which comprises administering an effective amount of the compound of claim 1 to human beings or animals.

11. A method for treating kidney dysfunction, which comprises administering an effective amount of the compound of claim 1 to human beings or animals.

12. A method for treating kidney dysfunction, which comprises administering an effective amount of $PGE_2$ antagonist to human beings or animals.

13. A method for treating kidney dysfunction, which comprises administering an effective amount of $EP_4$ receptor blocker to human beings or animals.

14. A method for treating mesangial proliferative glomerulonephritis, which comprises administering an effective amount of $PGE_2$ antagonist to human beings or animals.

15. A method for treating mesangial proliferative glomerulonephritis, which comprises administering an effective amount of $EP_4$ receptor blocker to human beings or animals.

* * * * *